US010695168B2

(12) United States Patent
Kozin et al.

(10) Patent No.: US 10,695,168 B2
(45) Date of Patent: Jun. 30, 2020

(54) PROSTHETIC DEVICES FOR SEMICIRCULAR CANAL DEFECTS

(71) Applicant: Massachusetts Eye and Ear Infirmary, Boston, MA (US)

(72) Inventors: Elliott Kozin, Boston, MA (US); Aaron K. Remenschneider, Boston, MA (US); Daniel J. Lee, Brookline, MA (US); Heidi Nakajima, Andover, MA (US); Song Cheng, Providence, RI (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 15/566,896

(22) PCT Filed: Apr. 15, 2016

(86) PCT No.: PCT/US2016/027916
§ 371 (c)(1),
(2) Date: Oct. 16, 2017

(87) PCT Pub. No.: WO2016/168718
PCT Pub. Date: Oct. 20, 2016

(65) Prior Publication Data
US 2018/0116788 A1    May 3, 2018

Related U.S. Application Data

(60) Provisional application No. 62/149,191, filed on Apr. 17, 2015.

(51) Int. Cl.
*A61F 2/18*          (2006.01)

(52) U.S. Cl.
CPC .......... *A61F 2/18* (2013.01); *A61F 2002/183* (2013.01); *A61F 2230/0052* (2013.01);
(Continued)

(58) Field of Classification Search
CPC .. A61F 2/18; A61F 2230/0052; A61F 2/2875; A61F 2002/2878; A61F 2002/2885; A61F 2002/2889; A61F 2002/30227; A61F 2002/30172; A61F 2002/183; A61B 2090/103
See application file for complete search history.

(56) References Cited

U.S. PATENT DOCUMENTS 6,304,787 B1   10/2001   Kuzma et al.
6,432,139 B1    8/2002   Elies et al.
(Continued)

OTHER PUBLICATIONS

International Search Report and Written Opinion in International Application No. PCT/US2016/027916, dated Sep. 2, 2016, 14 pages.
(Continued)

*Primary Examiner* — Brian A Dukert
*Assistant Examiner* — Rebecca Lynee Zimmerman
(74) *Attorney, Agent, or Firm* — Fish & Richardson P.C.

(57) ABSTRACT

This disclosure features elongated prosthetic devices that can be used to repair, e.g., resurface or occlude, a defect of a semicircular canal, e.g., a superior semicircular canal dehiscence, as well as methods of making and using these devices. For example, the devices can be made using three-dimensional (3D) printing.

16 Claims, 24 Drawing Sheets

(52) U.S. Cl.
CPC . *A61F 2240/002* (2013.01); *A61F 2250/0067* (2013.01); *A61F 2250/0098* (2013.01); *A61L 2300/406* (2013.01); *A61L 2300/41* (2013.01); *A61L 2300/414* (2013.01); *A61L 2300/426* (2013.01); *A61L 2300/43* (2013.01); *A61L 2300/44* (2013.01); *A61L 2430/14* (2013.01)

(56) References Cited

U.S. PATENT DOCUMENTS

| | | |
|---|---|---|
| 2004/0230254 A1 | 11/2004 | Harrison et al. |
| 2007/0027465 A1 | 2/2007 | Merfeld et al. |
| 2007/0208403 A1 | 9/2007 | Della et al. |
| 2011/0117197 A1* | 5/2011 | Emanuel ............... A61L 27/18 424/486 |
| 2012/0089237 A1* | 4/2012 | Vallittu ............... A61F 2/2803 623/23.72 |
| 2012/0226187 A1 | 9/2012 | Bierer et al. |
| 2012/0330427 A1* | 12/2012 | Yaremchuk ........... A61F 2/0059 623/17.18 |
| 2014/0228926 A1 | 8/2014 | Della et al. |
| 2016/0287339 A1* | 10/2016 | Bin Abdul Rahman ................. G09B 23/286 |

OTHER PUBLICATIONS

International Preliminary Report on Patentability in International Application No. PCT/US2016/027916, dated Oct. 26, 2017, 8 pages.

* cited by examiner

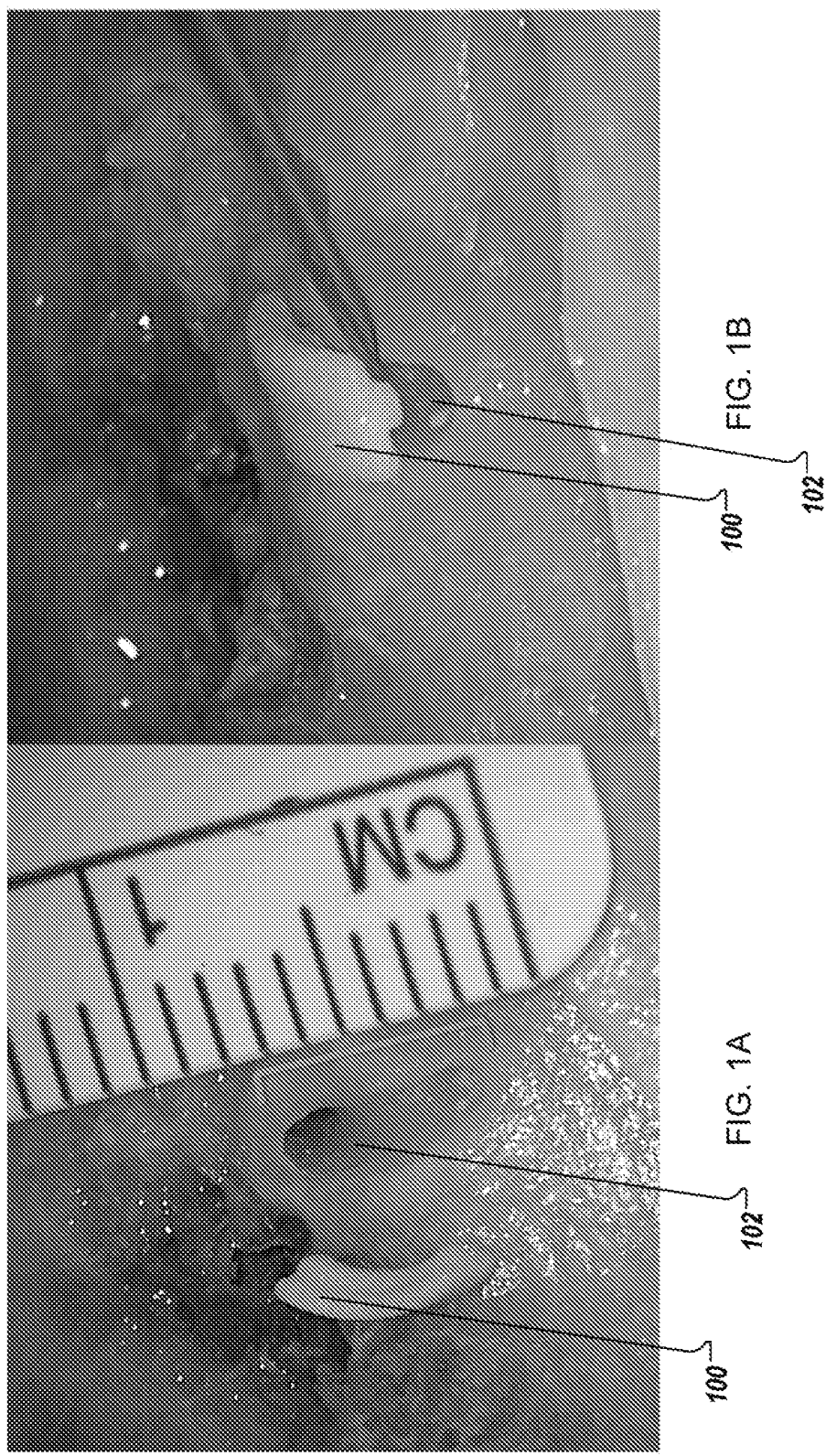

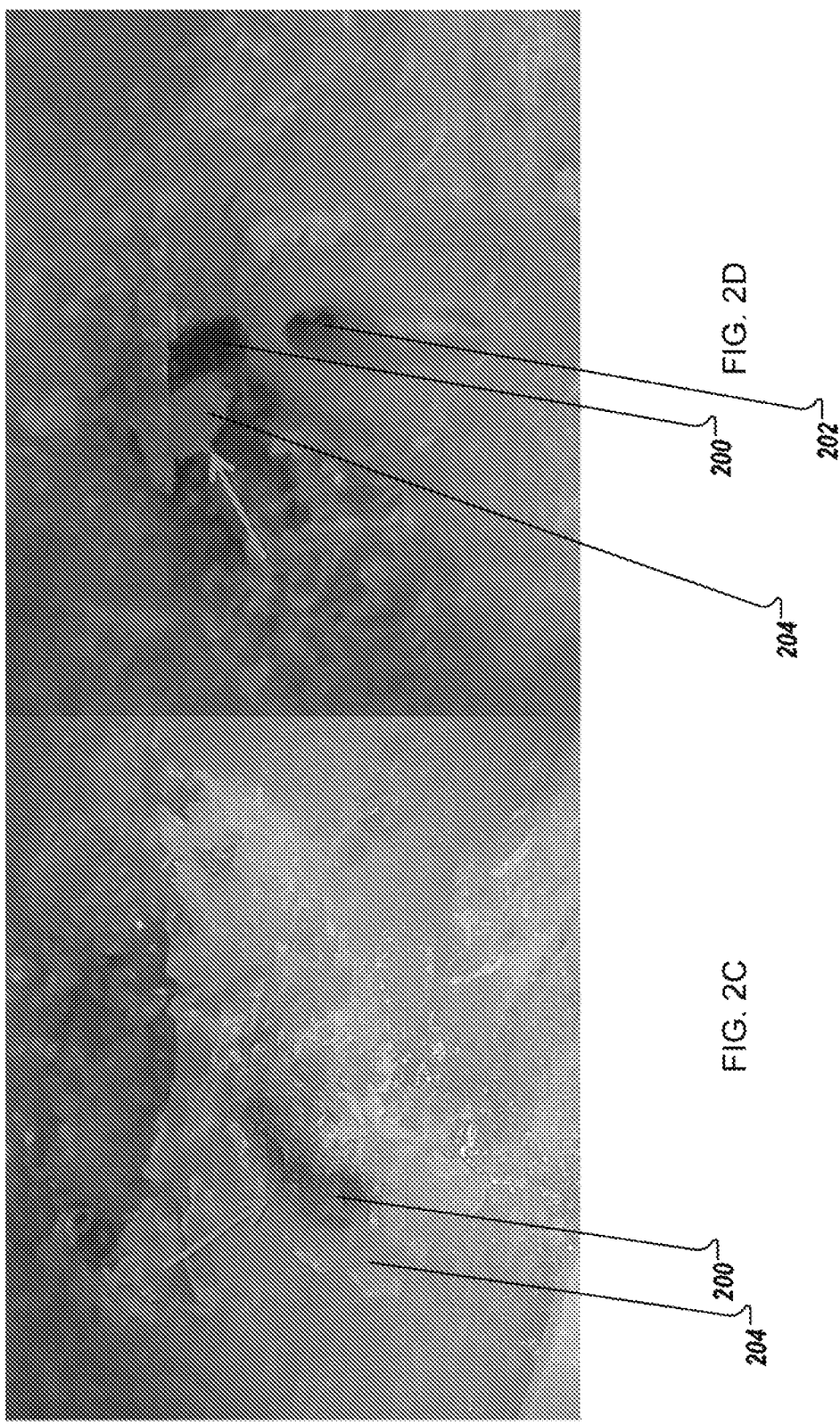

PROSTHETIC DEVICES FOR SEMICIRCULAR CANAL DEFECTS

CROSS-REFERENCE TO RELATED APPLICATIONS

This application is a § 371 U.S. National Phase Application of International Application No. PCT/US2016/027916, filed on Apr. 15, 2016, and claims the benefit of U.S. Provisional Patent Application Ser. No. 62/149,191, filed on Apr. 17, 2015. The entire contents of the foregoing applications are incorporated herein by reference.

FIELD OF THE INVENTION

The present document relates to prosthetic devices for the inner ear.

BACKGROUND OF THE INVENTION

The semicircular canals (SC) in the inner ear can develop various defects. For example, a dehiscence, e.g., a superior canal dehiscence (SCD), is a bony defect of the canal, e.g., the superior semicircular canal (SSC) that, when associated with vestibular and auditory complaints, is referred to as SCD syndrome (SCDS). Signs and symptoms of SCDS are believed to arise from a so-called "Third Window" phenomenon. Sound induced movement at the stapes footplate normally results in fluid movement through the high impedance cochlea. However, in SCD, a third window at the SSC results in shunting of inner ear fluids through the membranous labyrinth, towards this area of lower impedance. This results in auditory induced vestibular symptoms such as dizziness triggered by sound (Tullio's sign) or pressure (Hennebert's sign). Such dehiscence can also occur in the lateral and posterior semicircular canals.

A reduction in the pressure across the cochlear partition and an increase in bone-conducted, cochlear-evoked potentials lead to either hearing loss (seen as a low frequency air bone gap) or conductive hyperacusis (with "supra-normal bone conduction thresholds seen at −5 or −10 dB). Classic symptoms include aural fullness, pulsatile tinnitus, hyperacusis, and autophony, in addition to dizziness and vertigo. Surgical intervention is reserved only for patients with debilitating auditory and/or vestibular symptoms, because, as currently performed, this procedure carries a risk of partial or complete hearing loss in the affected ear, as well as persistent disabling dizziness or vertigo.

Several types of SCD repair have been described, and fall into two general categories: "resurfacing procedures" and "occluding procedures." Resurfacing is performed by placement of a bone chip, fascia, cartilage, bone cement, or another material directly over the defect, which effectively places a "cap" over the bony defect and attempts to "close" the third window without affecting the membranous inner ear. Occluding techniques are performed by placement of bone wax, bone chips, or fascia within the lumen of the canal to destroy the membranous inner ear and occlude both limbs of the canal, which effectively "plugs" the defect.

SUMMARY

This disclosure is based, at least in part, on the discovery that a few key measurements of a semicircular canal defect, e.g., a dehiscence, for example, a superior canal dehiscence (SCD), can be accurately determined using standard imaging techniques and used to create a set or kit of several pre-fabricated prostheses or a custom fabricated prosthesis that can then be used to repair a specific patient's semicircular canal defect in a surgery that can lower the risk of side effects when compared to current surgical methods. In some cases, these measurements can be converted directly into a few parameters that define the size and shape of a semicircular canal (SC) prosthesis, e.g., a superior semicircular canal (SSC) prosthesis. For custom-designed prostheses, rapid manufacturing like three-dimensional (3D) printing can provide a surgeon with a custom prosthesis quickly and economically.

Once placed, these prostheses have advantages over existing materials, such as fascia grafts, cartilage, bone wax, or bone chips. Due to the size and precise shape of these SC prostheses, graft or bone wax is prevented from entering the lumen of the superior semicircular canal. Post-operative imaging can also be improved by the use of radiopaque or similar materials in preparing the prostheses.

In one aspect, this disclosure features elongated prosthetic devices having a T-shaped cross section that includes an anchor portion and a wing portion and has a curved longitudinal axis. The anchor portion comprises a stem of the T-shaped cross section and extends along the curved longitudinal axis for at least a portion of the device. The wing portion comprises a horizontal top of the T-shaped cross section and extends along the curved longitudinal axis for at least a portion of the device. The anchor portion is narrower than the wing portion. The prosthetic devices are configured to be seated within a defect of a superior semicircular canal.

Implementations of the new devices can include any, all, or none of the following features. They can be configured to be seated in a defect of a superior semicircular canal, e.g., the anchor portion is configured to be seated in the defect, and the wing portion is configured to be wider than defect such that the wing portion is not able to fit within the defect. The prosthetic devices can be configured to not occlude the superior semicircular canal when the prosthetic device is seated in the defect. ("resurfacing prosthesis") The wing portion can include a lower concave surface configured to align with an outer surface of the superior semicircular canal to resurface the superior semicircular canal. The anchor portion can include an outer surface configured to align with an inner surface of the defect to seal the defect in the superior semicircular canal ("occluding prosthesis"). The prosthetic devices can be made of or can be made to include a material that can store and elute one or more agents into surrounding bone, blood, inner ear and/or tissue once the device is implanted in a patient. The agents can include at least one or a combination of a steroid, antibiotic, bisphosphonate, anesthetic agent, lidocaine, non-steroidal anti-inflammatory, immune-modulating drug, biologic drug, tumor necrosis factor (TNF) inhibitor, interleukin (IL)-6 inhibitor, IL-1 inhibitor, T cell mediator, an antibody, a chemotherapy agent, cyclosporine, methotrexate, glutamate antagonist, memantine, caroverine, magnesium, neurotropic factor, NeuroTrophin-3, and brain-derived neurotropic factor (BDNF).

In certain embodiments, the prosthetic devices can be manufactured from one or more of the following materials: polydimethylsiloxane (PDMS), hyaluronic acid (HA), poly (glycolic acid) (PGA), poly (lactic-co-glycolic acid) (PLGA), polylactic acid (PLA), polyurethane, collagen, fibrin, nylon, silk, poliglecaprone, elastin, titanium, platinum, aluminum, metal alloys, metal composites, and nitinol. The prosthetic device includes a radiopaque material. The defect may be a dehiscence.

In another aspect, this disclosure features prosthetic devices having a curved longitudinal axis and that are configured to be seated in a defect of a superior semicircular canal and to occlude one or both sides or "limbs" of the lumen within a superior semicircular canal.

Implementations of these new devices can include any, all, or none of the following features. The prosthetic devices can have a convex-shaped cross section. The convex-shaped cross section can be one of a trapezoid, a rectangle, and an oval. The prosthetic devices can also have a non-convex-shaped cross section. The prosthetic devices can be made of or include a material that can store and elute an agent into surrounding bone, blood, and tissue once the device is implanted in a patient. The agent includes at least one of a steroid, antibiotic, bisphosphonate, anesthetic agent, lidocaine, non-steroidal anti-inflammatory, immunomodulating drug, biologic drug, tumor necrosis factor (TNF) inhibitor, interleukin (IL)-6 inhibitor, IL-1 inhibitor, T cell mediator, an antibody, a chemotherapy agent, cyclosporine, methotrexate, glutamate antagonist, memantine, caroverine, magnesium, neurotropic factor, NeuroTrophin-3, and brain-derived neurotropic factor (BDNF). The prosthetic device includes at least one of polydimethylsiloxane (PDMS), hyaluronic acid (HA), poly(glycolic acid) (PGA), poly (lactic-co-glycolic acid) (PLGA), polylactic acid (PLA), polyurethane, collagen, fibrin, nylon, silk, poliglecaprone, elastin, titanium, platinum, aluminum, metal alloys, metal composites, and nitinol. The prosthetic device includes a radiopaque material. The defect is a dehiscence.

The present disclosure also features methods of generating a geometric model, the method includes receiving, by a computer system, first data that includes one or more images of a defect of a superior semicircular canal. The methods further include generating, by the computer system, second data from the first data, wherein the second data includes one or more measurements of the defect. The methods further include generating, by the computer system, third data from the second data, wherein the third data includes one or more prosthetic parameters that define at least some of the geometry of a prosthetic device. A geometric model of the prosthetic device is generated from the third data. The methods can further include outputting, by the computer system, the geometric model for fabrication.

Implementations of these methods can include any, all, or none of the following features. The methods can further include fabricating the prosthetic device using the geometric model. Fabricating the prosthetic devices can include three dimensional (3D) printing of the prosthetic device. The images of the first data can include at least one or both of a Pöschl view of the defect and a Stenvers view. The measurements of the defect can include at least one of a curve of the defect, a depth of the defect, and a width of the defect. The prosthetic parameters can include at least one of a curved longitudinal axis, a prosthetic depth, and a prosthetic width. The methods can include the one or more measurements of the defect including a curve of the defect, a depth of the defect, and a width of the defect; and the one or more prosthetic parameters can include a curved longitudinal axis that corresponds to the curve of the defect, a prosthetic depth that corresponds to the depth of the defect, and a prosthetic width that corresponds to the width of the defect. Generating the fourth data further can include modifying a template model according to the third data. Generating the fourth data can further include programmatically generating the geometric model using the third data as input. The defect may be a dehiscence In another aspect, this disclosure features methods of 3D printing prosthetic devices. The methods include receiving a build plan for a prosthetic device having a T-shaped cross section and that includes an anchor portion and a wing portion and having a curved longitudinal axis. In these methods, the anchor portion comprises a stem of the T-shaped cross section and extends along the curved longitudinal axis for at least a portion of the device. The wing portion comprises a horizontal top of the T-shaped cross section and extends along the curved longitudinal axis for at least a portion of the device. The anchor portion is narrower than the wing portion; and the prosthetic device is configured to be seated in a defect of a superior semicircular canal. The method further comprises 3D printing the prosthetic device according to the build plan. The defect may be a dehiscence In another aspect, the methods of 3D printing prosthetic devices include receiving a build plan for a prosthetic device having a curved longitudinal axis and being configured to be seated in a defect of a superior semicircular canal. Once seated in the defect, the prosthetic device is configured to occlude the superior semicircular canal. The methods can further include 3D printing the prosthetic device according to the build plan.

In another aspect, a kit contains two or more of the prosthetic devices described herein. In some implementation, at least two of the prosthetic devices have different geometry.

The use of the prosthetic devices as described herein can enable SC defect repairs, e.g., SCD repairs, with improved outcomes and a higher safety profile compared to prior known techniques described above. For example, an SC repair performed with a prosthetic device as described herein held in place with bone wax can result in the remediation or elimination of the risk of damage to the membranous labyrinth from pressure fluctuations during surgery and/or migration of graft material. By reducing the risk of these types of damage, use of these new prosthetic devices can greatly reduce the likelihood of hearing loss or other side effects. Additionally, the prosthetic devices can be configured in a way that allows for easier placement in surgery, as compared with use of a bone wax, bone chip, or fascia, which can be difficult to handle and may be prone to migration.

By fabricating the prosthetic device with a radiopaque material, intraoperative and postoperative imaging of the repair can be made feasible as the radiopaque material can be visible and repair can be assessed by computed tomography (CT) scan. By designing the prosthetic device based on a small number of parameters that correspond to measurements of a patient's SC defect, e.g., an SCD, an appropriate sized prosthesis can be easily selected or designed. Rapid and flexible fabrication techniques such as 3D printing can allow for custom-designed prosthetic devices based on a particular patient's SC defect, e.g., SCD.

Particular advantages of an SC prosthesis, e.g., an SSC prosthesis, as described herein include its relatively rigid, fixed length. The prosthesis, unlike bone wax, fascia, bone chips, etc., does not have the potential for intraluminal migration. This could decrease both short and long-term complications of surgery using current techniques. The prosthesis will also enable a customized, personalized design to fit a particular patient's anatomy. A customized design enables a better "seal," reducing the effects of the "Third Window" phenomenon. The new prostheses can also be readily placed without concern for over plugging or questionable stability of repair, unlike the challenges that bone wax, fascia, cartilage, and bone chips currently present. These materials require multiple applications and are often difficult to handle within the surgical field. The new prostheses also avoid the need for currently used prosthetic repair materials and thus would limit any morbidity associated with the harvest of autologous tissue, such as fascia or bone, and should also expedite surgery.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A and 1B are photographic representations that show an example of a resurfacing prosthetic device placed in a superior semicircular canal dehiscence.

FIGS. 2A, 2B, 2C, and 2D are photographic representations that show an example of an occluding prosthetic device placed into the limbs of the superior semicircular canal through a dehiscence.

Like reference symbols in the various drawings indicate like elements

DETAILED DESCRIPTION

Semicircular canal (SC) prostheses used to repair defects, such as a dehiscence, of the SCs, are described, along with methods for manufacturing such prostheses, uses of such prostheses, and the results of tests of such prostheses Canal Defect Prosthesis Overview The prosthetic devices described herein can be used to repair, e.g., resurface or occlude, a defect in a semicircular canal, such as a dehiscence, of the superior, posterior, or lateral semicircular canal. The prostheses can be designed or selected to match the geometry of the defect, e.g., dehiscence, and can be surgically placed either into the dehiscence in the case of resurfacing surgery, or into the canal through the dehiscence in the case of an occluding surgery. The prosthesis can then be held in place with a media, for example bone wax.

Figure 2A:
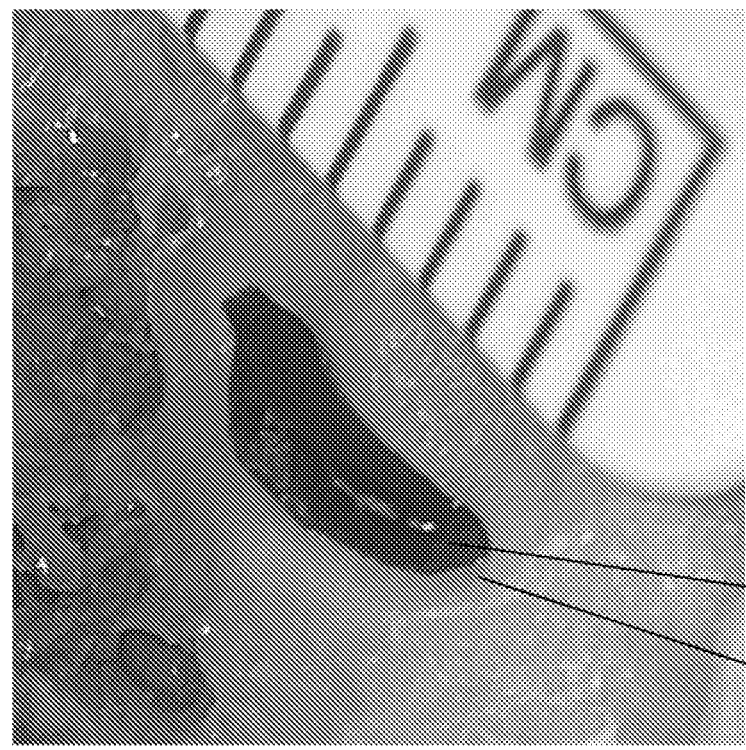
Figure 2B:
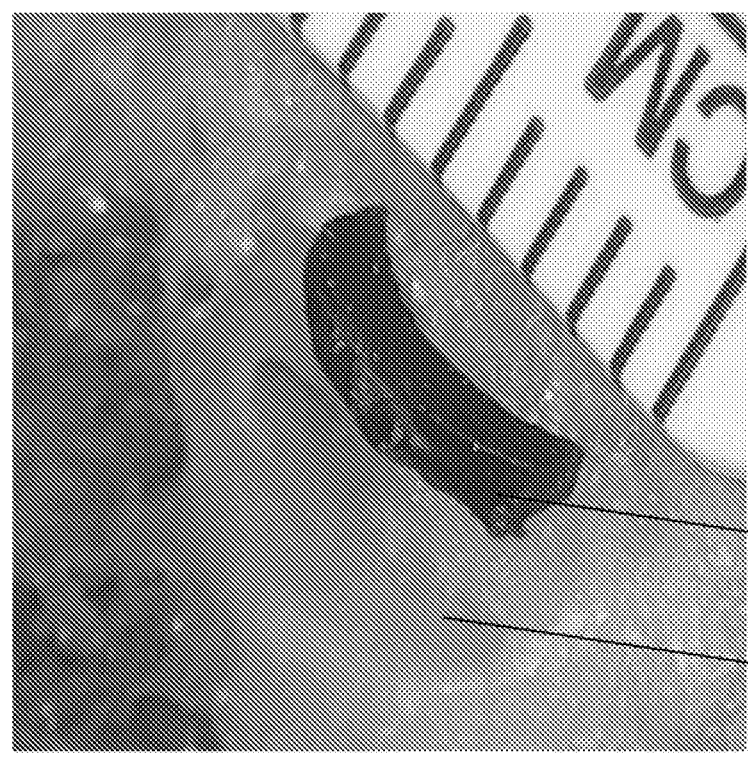

FIGS. 1A and 1B show an example of a resurfacing prosthesis 100 placed in a cadaveric superior canal dehiscence 102. In other examples, a similar prosthesis can be placed in a posterior or lateral semicircular canal. As can be seen here, the resurfacing prosthesis has a curved lateral axis and a T-shaped cross section. The upper portion of the T, which will be referred to as the wings, are configured to sit above the dehiscence on the surface of the semicircular canal, re-establishing a fixed closure over the canal. Anatomically, this is along the middle fossa floor of the skull base which is covered with overlying dura and brain. The lower portion of the T, which will be referred to as the anchor, is configured to sit within the dehiscence FIGS. 2A and 2B show an example of an occluding prosthesis 200 placed into a superior canal through a dehiscence 202. Similar to the resurfacing prosthesis 100, the occluding prosthesis 200 has a curved lateral axis. In contrast with the resurfacing prosthesis 100, the occluding prosthesis 200 has a rectangular, instead of a T-shaped, cross section. As can be seen, the prosthesis 200 is placed into the superior canal in order to occlude the superior canal.

Once placed, either prosthesis 100 or 200 may then be secured in place. For example, a media such as bone wax or bone cement can be used to cover the prosthesis, securing it to the surrounding skull base to stably lock it in place. Media used to secure the prosthesis in place would be unable to enter the canal, but would instead ground the prosthesis along the floor of the middle fossa. FIG. 2C shows the occluding prosthesis 200 secured with a layer of bone wax 204. FIG. 2D shows the occluding prosthesis 200 removed from the dehiscence 202. No bone wax 204 was identified in the dehiscence 202.

Resurfacing Prostheses

In general, the goal of a semicircular canal, e.g., superior semicircular canal resurfacing procedure is to resurface the temporal bone, closing the canal dehiscence without damaging the inner ear or stopping luminal flow within the canal. The resurfacing prostheses are designed to sit within the dehiscence deep enough to close the dehiscence without occluding the lumen of the canal and without applying undue pressure on the membranous labyrinth within.

Figure 3A:
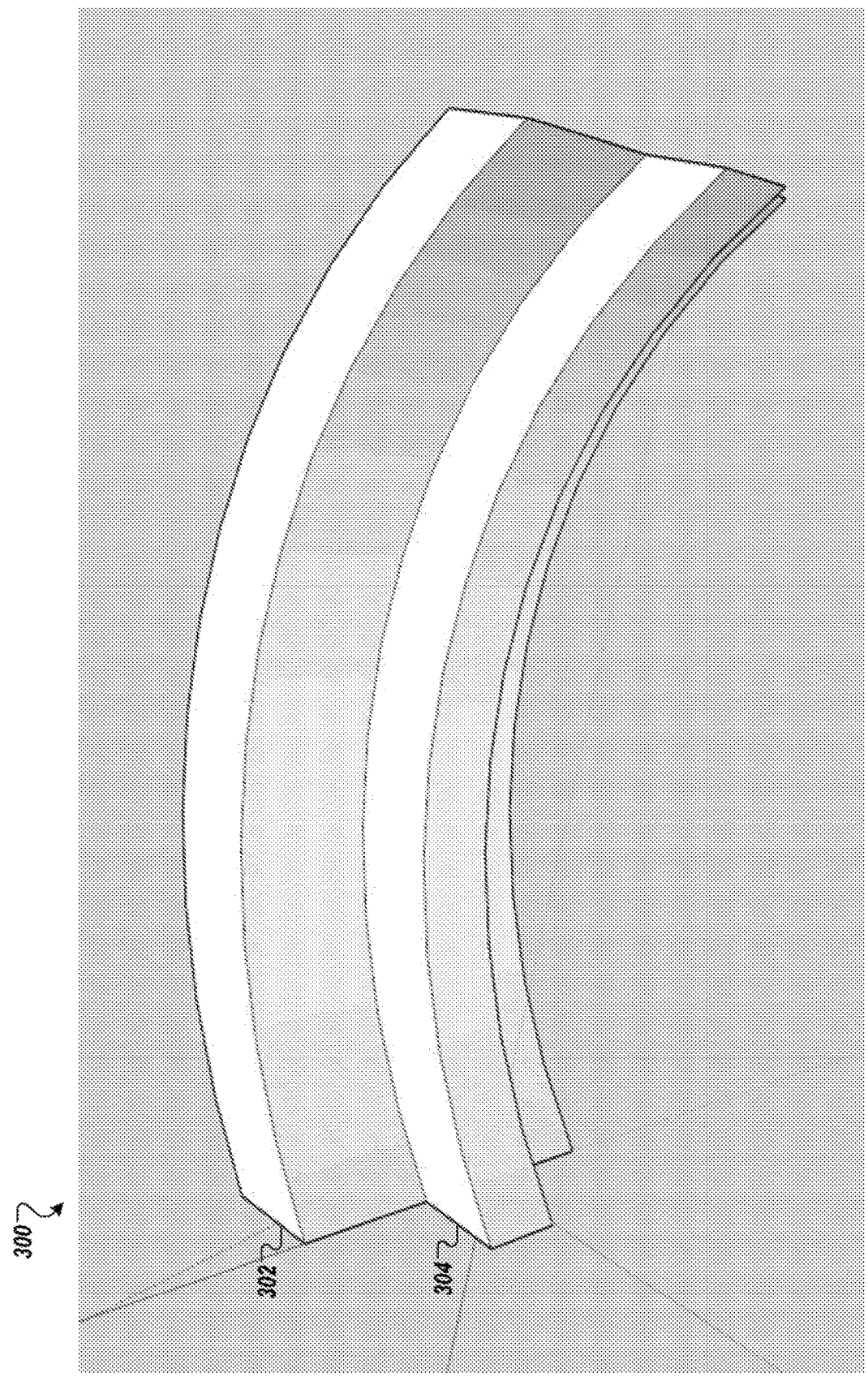
FIGS. 3A, 3B, and 3C are schematic diagrams that show isometric, top, and side views of an example of a resurfacing prosthesis.
Figure 3B:
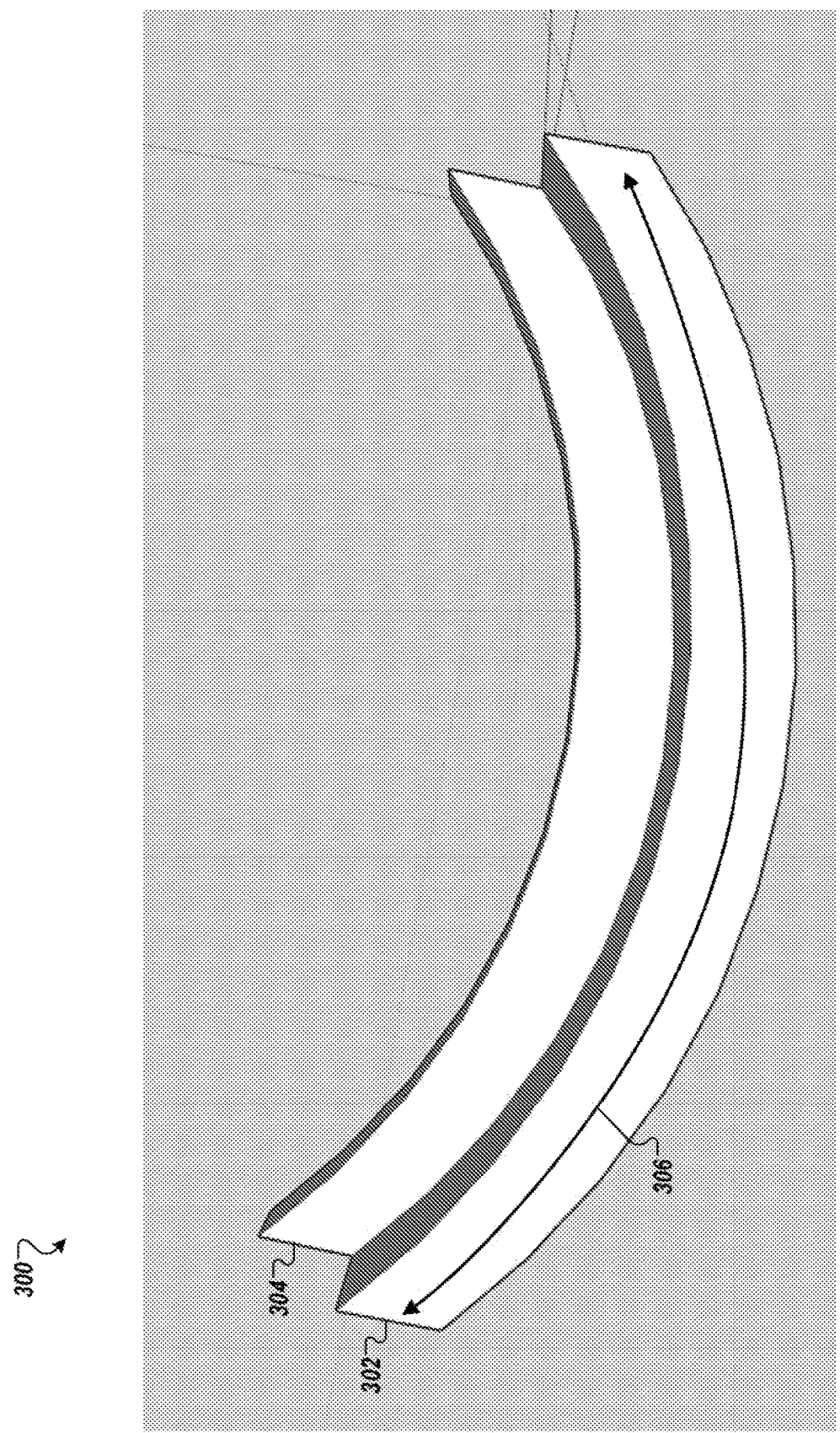
Figure 3C:
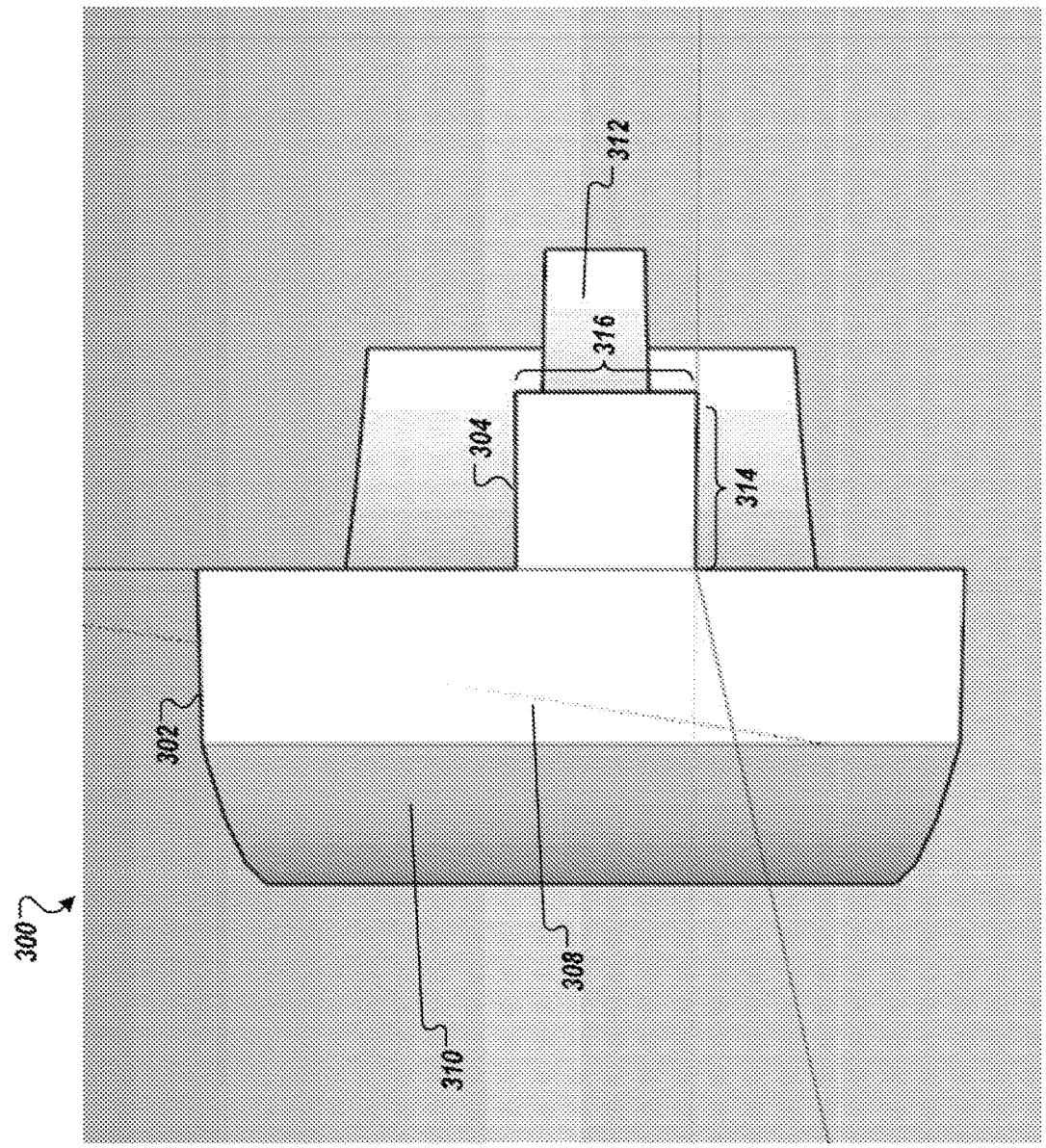

FIGS. 3A, 3B, and 3C show isometric, top, and side views of an example of a resurfacing prosthesis 300. The views shown are using a perspective projection, not a parallel projection.

The resurfacing prosthesis 300 includes a wings section 302 and an anchor portion 304. In general, the wings section 302 is configured so that it sits on the surface of the canal when placed, with the smaller anchor section 302 sitting within the defect in the bony canal to secure the resurfacing prosthesis 300 without occluding the lumen of the canal.

The resurfacing prosthesis 300 is formed along a curved longitudinal axis 306, shown in FIG. 3B. The face 308 of the resurfacing prosthesis 300 can be formed in a T-shape. Similarly, cross-sections of the resurfacing prosthesis 300 can have the same or a similar T-shape.

The curve of the longitudinal axis 306, as well as the length of the longitudinal axis 306 (and therefore the curve and length of the resurfacing prosthesis 300) can be altered to control the size and shape of the resurfacing prosthesis 300. Similarly, the particular size and shape of the face 308, including either or both of the wings 302 and the anchor 304, can be altered to control the size and shape of the resurfacing prosthesis 300. For example, the size and curve the longitudinal axis 306 and the size of the wings 302 and the size of the anchor 304 can be based on measurement of a particular dehiscence of an individual patient. In another example, a kit with prostheses of various sizes and curves can be provided so that a prosthesis with the closest fit to a particular patient's dehiscence and canal size and shape can be selected. For example, in some cases, preoperative imaging may not be available. These cases include operations in countries where imaging devices are not readily available or cost effective. In such cases, the use of a kit of prostheses of potential sizes and shapes may be made available for sizing and selection during the operation.

When placed in a dehiscence, the upper surface 310 of the wings 302 generally aligns with the outer surface of the superior canal bone to form a new outer surface. Similarly, the inner surface 312 of the anchor 304 generally aligns with the inner surface of the superior semicircular bone to form a new inner surface, closing defect in the bony superior semicircular canal without damaging the membranous labyrinth.

In general, the anchor 304 can have a depth 314 and a width 316. The depth 314 can be configured to be less than the depth of the wall of a patient's canal, and the width 316 can be configured to be approximately the same size as a dehiscence. For example, this configuration can result in an anchor 304 that can fit securely in the dehiscence without occluding the canal.

Occluding Prostheses

In general, the goal of a semicircular canal, e.g., superior semicircular canal occluding procedure is to place an occluding prosthesis within the lumen of the semicircular canal, plugging both of the so-called "limbs" of the canal, e.g., on either side of the opening in the canal wall The occluding prosthesis is designed to fit within the dehiscence and protrude deep enough through the opening to plug both limbs of the superior semicircular canal, while taking care not to enter either the area of the crus commune, where the superior canal joins the posterior canal, or the ampulla of the superior canal, where the superior vestibular nerve originates.

Figure 4A:
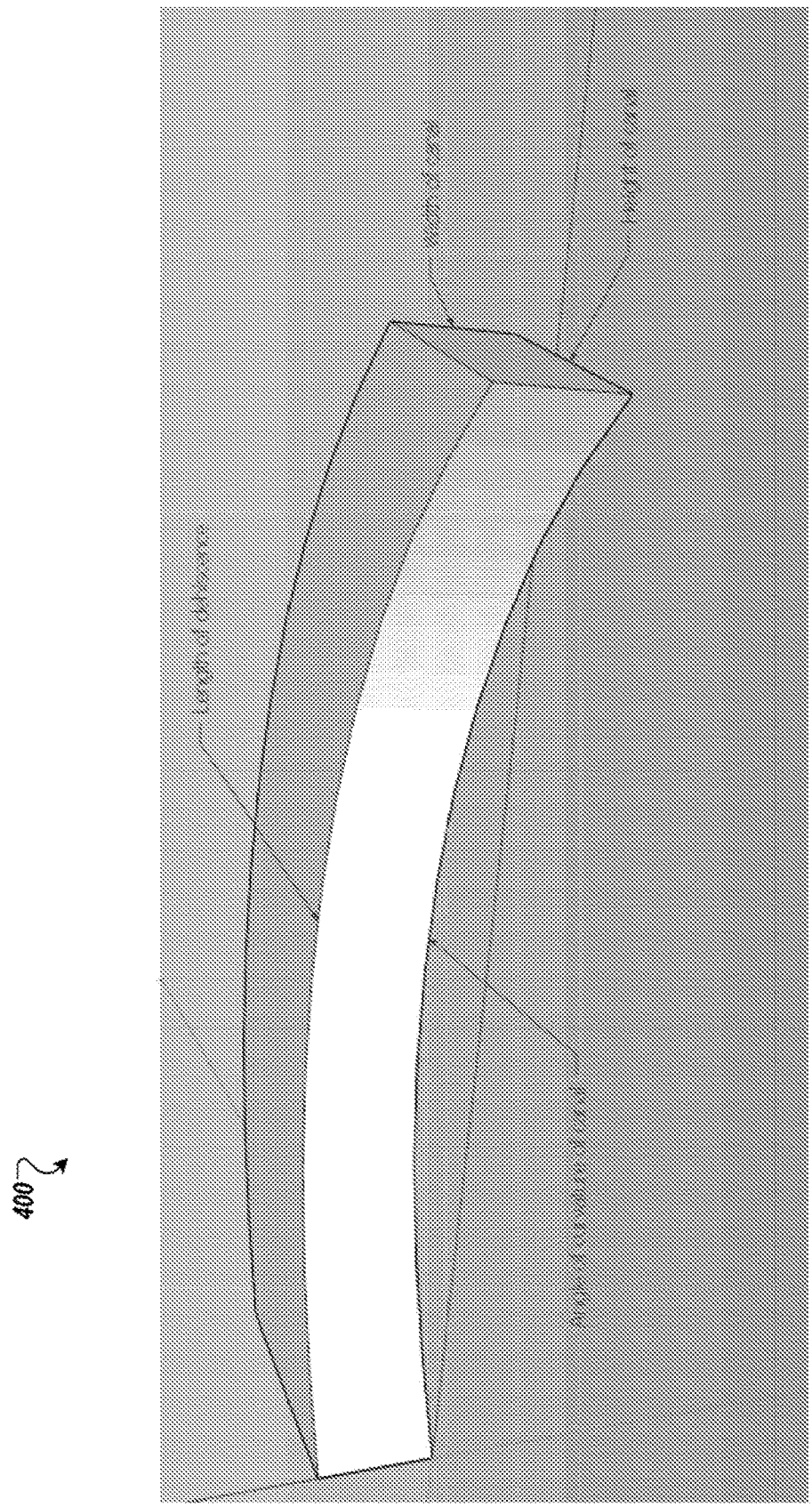
FIGS. 4A, 4B, and 4C are schematic diagrams that show isometric, top, and side views of an example an example of an occluding prosthesis.
Figure 4B:
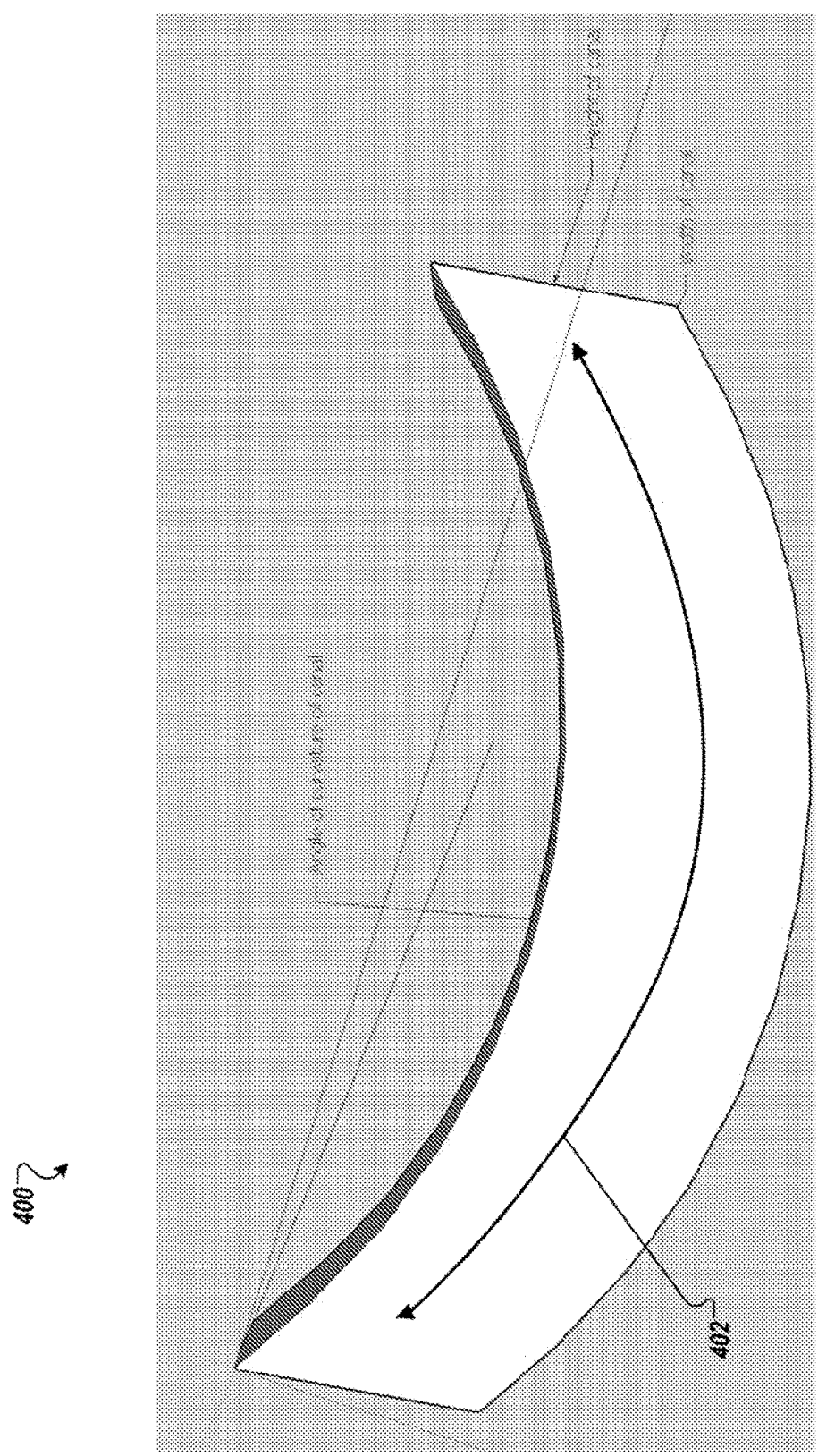
Figure 4C:
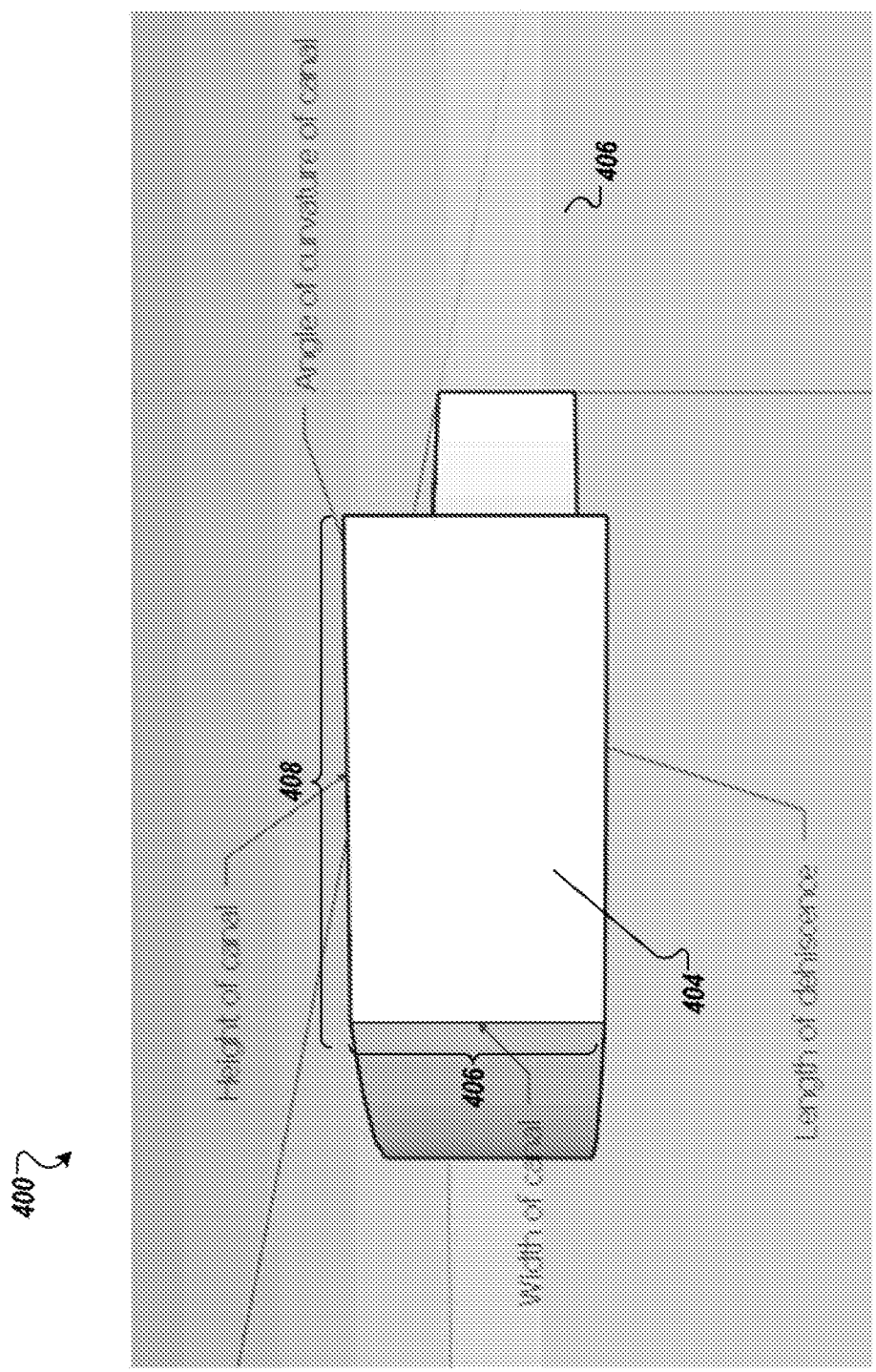

FIGS. 4A, 4B, and 4C show isometric, top, and side views of an example of an occluding prosthesis 400. The views shown are using a perspective projection, not a parallel projection.

Similar to the resurfacing prosthesis, the occluding prosthesis 400 is formed along a curved longitudinal axis 402, shown in FIG. 4B. The curve of the longitudinal axis 402, as well as the length of the longitudinal axis 402 (and therefore the curve and length of the occluding prosthesis 400) can be altered to control the size and shape of the occluding prosthesis 400. For example, the size and curve the longitudinal axis 402 can be based on measurements of a particular dehiscence of an individual patient. In another example, a kit with prostheses of various sizes and curves can be provided so that a prosthesis fitting a particular patient's dehiscence can be selected.

The face 402 of the occluding prosthesis 400 can be formed in a trapezoid, as shown here, or in other shapes such as a circular/tubular shape, a square shape, etc. Similarly, cross-sections of the occluding prosthesis 400 can have the same or a similar shape. The particular size and shape of the face 402, can be altered to control the size and shape of the occluding prosthesis 400. For example, the size of the face 402 and the interior angles of the face 402 can be based on a measurement of a particular dehiscence of an individual patient. In another example, a kit with prostheses of various sizes and curves can be provided so that a prosthesis fitting a particular patient's dehiscence can be selected.

When placed in a dehiscence, the face 404 and the other face 406 can each be exposed to one side of the superior semicircular canal, plugging both limbs. In general, the face 404 can have a depth 406 and a width 408. The depth 406 can be configured to be the same as or greater than the depth of a patient's canal, and the width 316 can be configured to be approximately the same size as a dehiscence. For example, this configuration can result in an occluding prosthesis 400 that can fit into a dehiscence and plug both limbs of the canal. In some cases, the prosthesis 400 may be gently bent such that either end of the prostheses 400 are inserted in the limbs of the defect. Additionally or alternatively, the dehiscence may be surgically opened to allow the prostheses 400 to be placed properly.

Method of Designing the Prostheses

As previously stated, the size and shape of both resurfacing and of occluding prostheses can be based on measurements of particular dehiscence, or based on ranges of potential measurements of potential dehiscences. Below will be described the use of measurements of a dehiscence for purposes of designing a particular prosthesis. This process can be used to design a personalized prosthesis for a particular patient, or as one of many designs intended to cover a range of possible dehiscences.

Both resurfacing prostheses and occluding prostheses can be defined with just a few parameters. It is possible to configure these parameters to correspond to measurements of the geometry of a dehiscence. In doing so, prostheses can be defined based on measurements taken from medical imaging.

Figure 5:
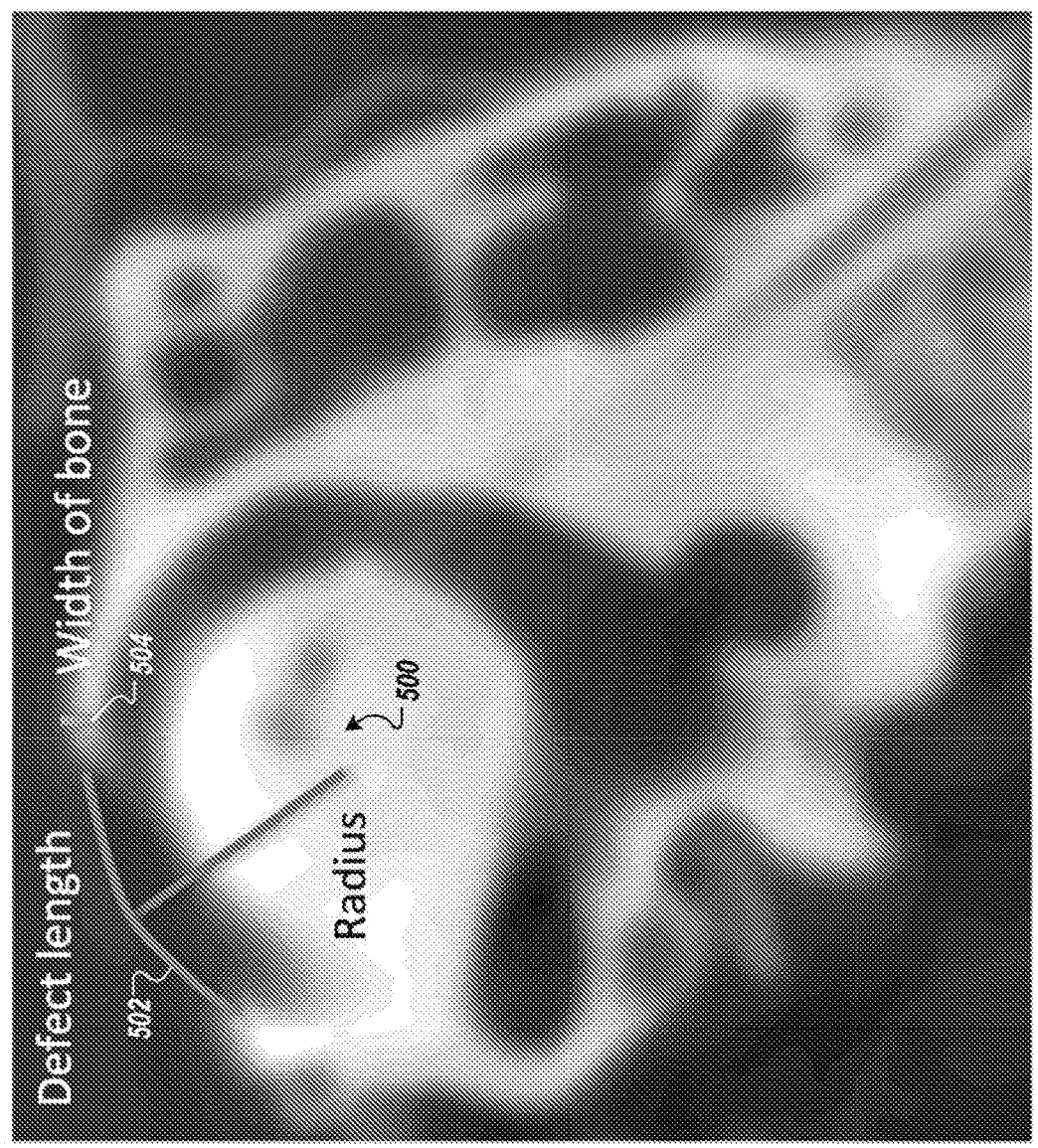
FIG. 5 is a computed tomography (CT) image that shows a Pöschl view (parallel) of an example of a temporal bone demonstrating superior semicircular canal dehiscence.

The resurfacing prostheses and the occluding prostheses both include a curved longitudinal axis. The length and curve of the prosthesis can be determined based on a measurement of a dehiscence. FIG. 5 shows a Pöschl view (parallel), CT image of a temporal bone demonstrating superior semicircular canal dehiscence 500. A Pöschl view is essentially an en face reconstructed view of the semicircular canal. It can offer a single image view of the entire circle of the canal. The use of Pöschl views provides a way that radiologists and otolaryngologists can rapidly determine if is any dehiscence exists, which may be difficult to identify in other radiographic views. From this image, a curve 502 can be created, showing where, for example, the outer surface of the superior bone would be if the dehiscence had not occurred. Additionally or alternatively, a measurement 504 of the bone width may be made.

From the curve 502, a curved longitudinal axis can be calculated for an SSC prosthesis. As one example, the exact size and shape of the curve 502 can be used as the longitudinal axis. As another example, the curve 502 can be altered to create a longitudinal axis. This can be preferable, for example, to account for the fact that a prosthesis must fit within the dehiscence, and thus must be slightly smaller than the dehiscence. The curve 502 may be defined as a length and radius as shown here, or any other technologically appropriate format of defining an arc or a curve.

The width of the bone may be measured with measurement 504. The measurement 504 may be used for example, as the maximum size of anchor depth for a resurfacing prosthetic. By limiting the anchor to the measurement 504, accidental occlusion of the canal by the anchor may be avoided.

Figure 6A:
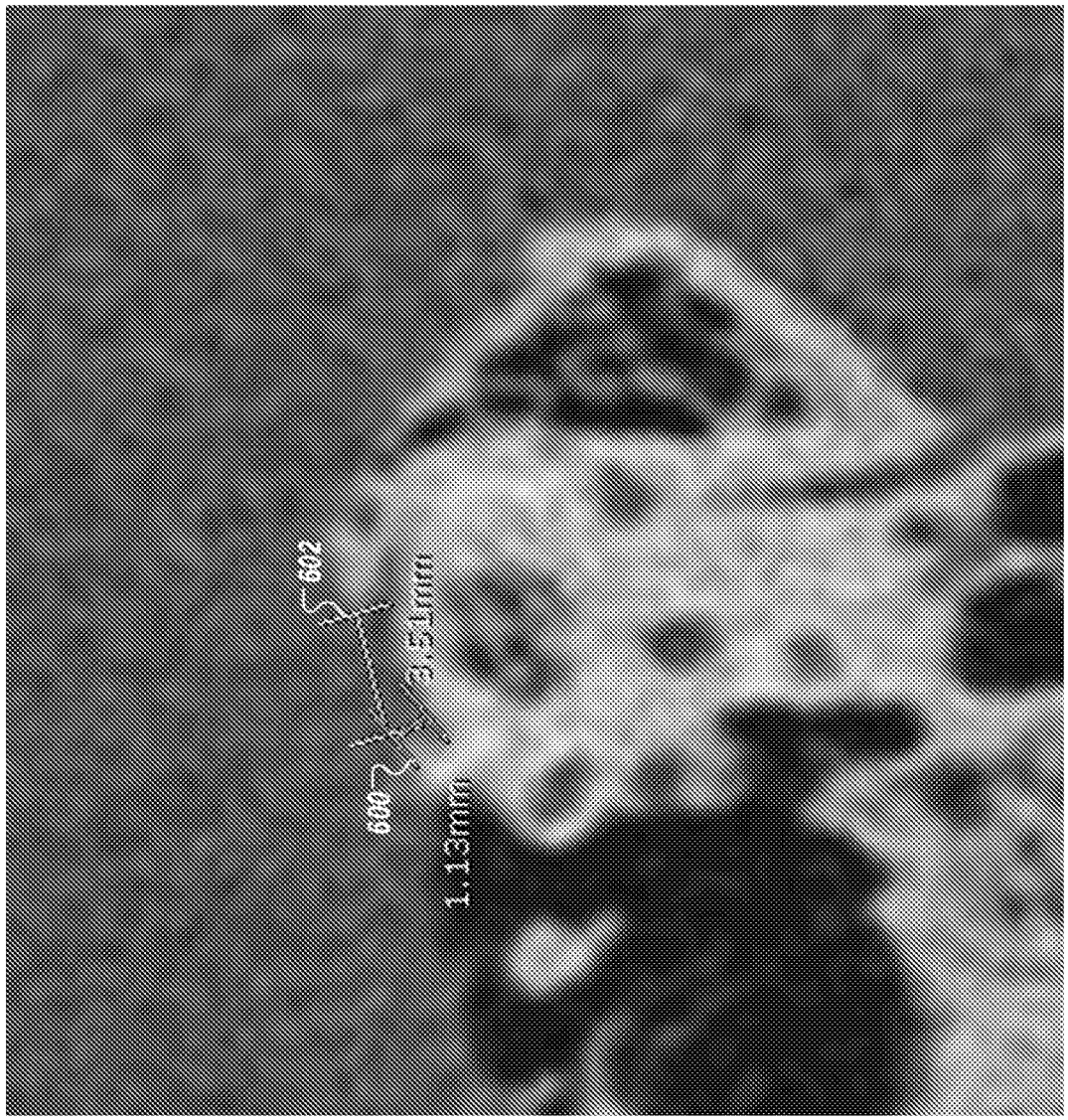
FIGS. 6A and 6B are CT images of an example of a temporal bone demonstrating superior semicircular canal dehiscence in various cross sections.
Figure 6B:
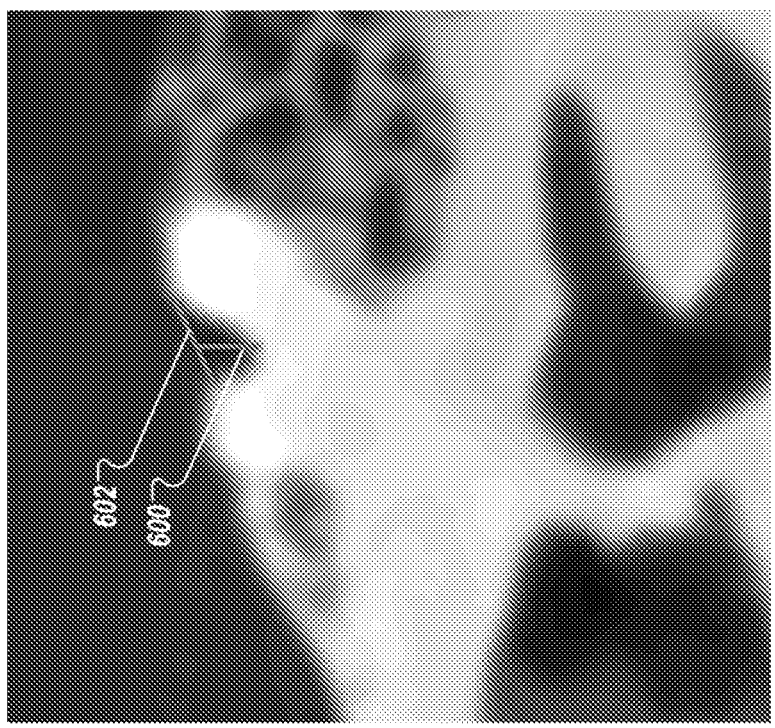

In addition to finding the size and shape of a longitudinal axis, imaging of a dehiscence can be used to find the size and shape for the faces (and corresponding cross-sections) of a prosthesis. FIG. 6A shows a Pöschl view, CT image of an example of a temporal bone demonstrating superior semicircular canal dehiscence. FIG. 6B shows a Stenver's view (perpendicular to the defect), CT image of temporal bone demonstrating superior semicircular canal dehiscence. A Stenver's view is orthogonal to a Pöschl view and shows a single image along the axis of the canal, demonstrating the cross sectional area of the canal. Images can be scrolled through to evaluate the entire length and cross sectional area of the canal along its axis. Measurement 600 is a measure of the canal depth and measurement 602 is a measure of the defect length.

The measurements 600 and 602 can be used to define parameters of a resurfacing prosthesis and/or of an occluding prosthesis that is personalized or measured to fit the specific patient's needs. For example, for a resurfacing prosthesis, the width and depth of the anchor portion of the prosthesis can be set to match the measurement 602 (so the anchor can be press-fit into the dehiscence) and less than the measurement 600 (so that the anchor does not occlude the canal). For an occluding prosthesis, the width and depth of the occluding prosthesis can be set to match the measurement 602 (so that the prosthesis fits in the dehiscence) and be the same or greater than the measurement 600 (so that the prosthesis plugs the canal).

In some configurations, the measurements and conversion to parameters of a prosthesis can be performed by a human operator. For example, a computer program can display images of a dehiscence, and the operator can use a software-based measurement tool to make measurements of the dehiscence. The same or a different human operator can then convert, either manually or with software tools, the measurements into parameters for one or more prostheses. These parameters (e.g., curve, depth, and width) can then be used by the same or a different human operator to define the size and shape of one or more prostheses. For example, the operator can adjust a template of a solid model file based on the parameters.

In some configurations, software tools can be provided to a human operator to partially automate this process under the operator's supervision and control. For example, a feature-extraction tool can pre-process the medical images and prepare provisional measurement values for display to a human operator. The human operator can then accept the provisional measurements, or can reject or adjust the provisional measurements. Once finalized, the software tool can then export the measurements to a solid modeling program configured to generate a solid model file of a prosthesis based on the received measurements.

Figure 7:
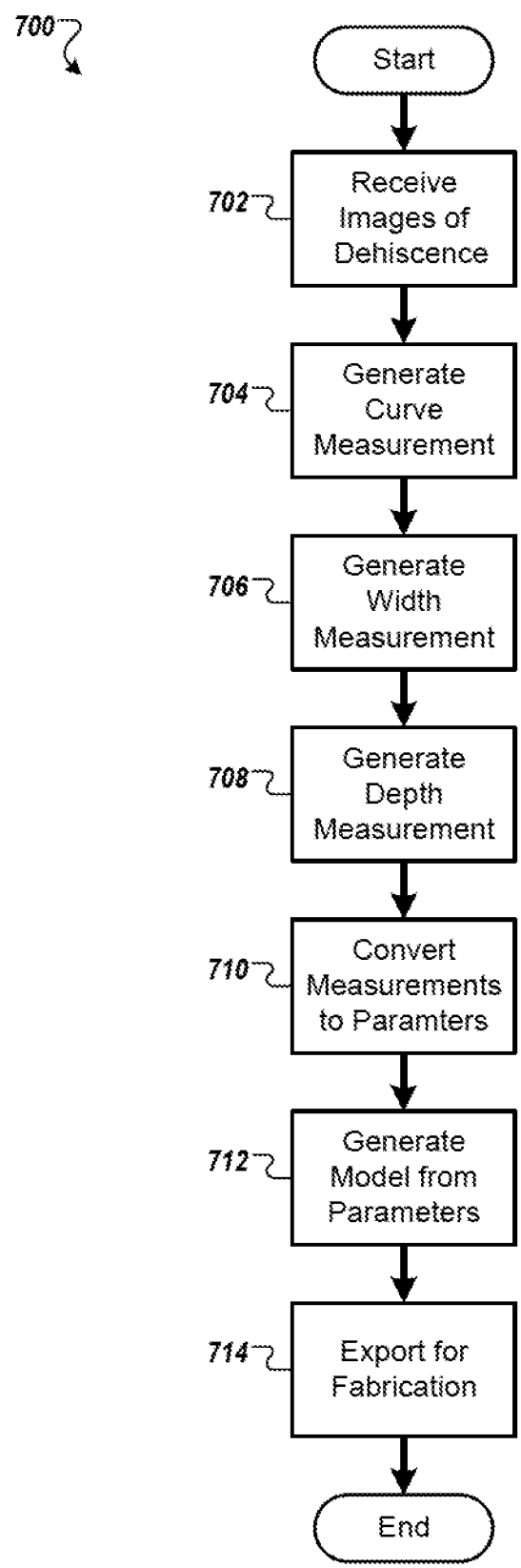
FIG. 7 is a flow chart of an example of a process for generating a prosthetic device as describe herein from images of a dehiscence.

In some configurations, the measurement and design process can be wholly or mostly automated. FIG. 7 shows an example of a flow chart of a process 700 for generating a model of a prosthesis from images of a dehiscence. For clarity, the process 700 will be described as an automatic process carried out by one or more computing devices. However, appropriate user review, correction, and control of any and all portions of the process 700 are possible. Additionally, the process 700 can be a portion of a larger workflow. For example, the process 700 can be repeated for a batch of images, resulting in a batch of models ready for fabrication.

The process 700 generally takes one or more images of a dehiscence and generates one or more models suitable for use in fabrication of a prosthesis. The process 700 can be performed for a particular patient pre-operatively. That is, the process 700 can be performed before an operation so that a patient-specific prosthesis is fabricated before the patient undergoes surgery. In some cases, the process 700 can be performed intra-operatively. That is, the process 700 can be performed during a patient operation. This can be necessary, for example, if the operation includes changing the shape of the dehiscence. For example, a dehiscence can have a jagged opening that is to be smoothed out before placement of a prosthesis. In this case, preoperative imaging may not be sufficient to create a prosthesis of the appropriate size and shape.

Images of a dehiscence are received (step 702). For example, a software tool with feature-extracting capabilities can receive a pre-configured image or images that show a dehiscence in one or more predefined views. The images can be pre-processed, for example to verify that they are of the correct file size and resolution, to increase contrast, or otherwise prepare the images for feature extraction.

A curve measurement is generated (step 704). For example, the feature extraction element of the software can identify elements of the dehiscence and/or superior bone and/or superior semicircular canal. From these identified elements, the software can generate a curve covering the missing portions of the superior bone and store data defining the curve (e.g., length, spline features).

A width measurement is generated (step 706) and a depth measurement is generated (step 708). For example, from one or more images of the dehiscence and/or superior bone and/or superior semicircular canal, the feature extraction element of the software can generate a depth and width measurement.

The measurements are converted to parameters (step 710). For example, the software processes the measurements to generate parameters for defining a solid model of a prosthesis. In some cases, this processing can include converting measurement formats (e.g., changing measurement units, rounding values to account for different precision levels). In some cases, this process can include changing the values (e.g., increasing a width measurement so that a prosthesis anchor presses against the sides of a dehiscence).

A model is generated from the parameters (step 712) and exported for fabrication (step 714). For example, the software tool can generate a solid model based on the parameters. In some configurations, the solid model can be generated by adjusting a template solid model so that the generated model has features matching the parameters. In some configurations, the solid model can be generated programmatically where the parameters are used as parameters of one or more functions whose output is a solid model. Once generated, the solid model can be sent to a fabrication facility. For example, the solid model can be transmitted over a computer network to a 3D printer or other fabrication machine.

Methods of Fabricating the Prostheses

Once a size and shape of a prosthesis is defined, any technologically appropriate form of fabrication can be used to fabricate one or more copies of the prosthesis. One example fabrication technique is three-dimensional (3D) printing. Other examples of such fabrication techniques include, but are not limited to, casting, end-milling, and extrusion.

Three-dimensional (3D) printing is a type of additive manufacturing in which a desired 3D shape or object is built up from an available supply of material. In some cases, the material is initially a solid that is temporarily melted, a liquid that is solidified, or a powder that is solidified during the manufacturing process. Examples of 3D printing techniques include stereolithography, in which a photo-responsive resin is hardened with a laser; fused deposit modeling (FDM), in which a solid material is melted, printed, and fused to surrounding material when solidified; filamentary extrusion/direct ink writing, in which the ink is extruded from a nozzle head via pressure and the resultant object can be cured or sintered; and granular material binding, in which a bed of granular material is bound, often with heat or a fluid binder.

A variety of 3D printing techniques and materials can be used to fabricate an SCD prostheses. In many cases, 3D printing can have a resolution finer than the resolution of the images from which the prosthesis is designed. 3D printing is possible with a variety of materials, which can result in prostheses with a variety of properties.

Some examples of materials that can be used include, but are not limited to, polydimethylsiloxane (PDMS), hyaluronic acid (HA), poly(glycolic acid) (PGA), poly (lactic-co-glycolic acid) (PLGA), polylactic acid (PLA), polyurethane, collagen, fibrin, nylon, silk, poliglecaprone, elastin, and metal-based materials. Metal-based materials include, but are not limited to, titanium, platinum, aluminum, alloys, and/or composites such as nitinol. Additionally, prostheses can be printed from a combination of two or more different materials.

Materials can be selected based on one or more properties that the materials impart to a fabricated prosthesis. For example, a radiopaque material (e.g., titanium) can be mixed into a less-radiopaque material (e.g., PDMS) to increase the visibility of a prosthesis when the prosthesis and surrounding anatomy is imaged either intra- or postoperatively.

In another example, the material or materials can be selected based on their mechanical properties. A deformable prosthesis (e.g., made from fibrin and silk) may be desired for a particular occluding prosthesis so that the prosthesis can be placed within the dehiscence and then expand within the canal. Alternatively, a more rigid prosthesis (e.g., made from a metal or hyaluronic acid) may be desired for a particular resurfacing prosthesis to ensure that the prosthesis does not impinge upon the sensitive membranous labyrinth of the semicircular canal.

In some cases, two or more materials may be used to fabricate a prosthesis. For example, for a resurfacing prosthesis, the anchor may be made of one material (e.g., titanium) while the wings are made of a different material (e.g., hyaluronic acid).

Additional material can be added to the printing material. For example, a dye, e.g., green or blue dye or a fluorescent or "neon" dye, can be added to increase the visual contrast of the prosthesis against blood, bone, and tissue. An RFID chip and antenna can be sunk into the prosthesis to track and/or uniquely identify the prosthesis. A drug or drug eluting material can be added to the prosthesis so that the prosthesis elutes a drug to the inner ear after being implanted. Examples of drugs to be delivered include, but are not limited to, steroids (e.g., dexamethasone), antibiotics (e.g., ciprofloxacin), bisphosphonates, anesthetic agent (e.g., lidocaine), non-steroidal anti-inflammatory, immunomodulating drugs (e.g., biologics, TNF inhibitors, IL-6 inhibitor, IL-1 inhibitor, and T cell mediators), antibodies that target inflammatory cells (e.g., B cells and cellular adhesion molecules), and chemotherapy agents (e.g., cyclosporine and methotrexate), glutamate antagonists (e.g., memantine, caroverine, and magnesium), and neurotropic factors (e.g., NeuroTrophin-3 and brain-derived neurotropic factor (BDNF)).

Uses and Methods of Implanting Prostheses

The prostheses described herein can be used for any appropriate resurfacing or occluding operations for the reconstruction of the skull base overlying the superior, posterior, or lateral semicircular canal or for the superior, posterior, or lateral semicircular canal itself.

The repair of SCD may occur via one of several approaches, including the transmastoid approach and the middle cranial fossa approach. The middle cranial fossa approach is most commonly utilized and described: The patient is positioned supine on the operating room table. Following intubation and a minimal hair shave, a 6-7 cm curvilinear incision is drawn, extending from 1 cm posterior and superior to the post-auricular skin crease and curving anteriorly along the line of the floor of the middle fossa and extending superiorly over the temporalis staying within hairline anteriorly. An appropriate volume of 1% lidocaine with 1:100,000 epinephrine (or an equivalent local anesthetic) is infiltrated into the planned surgical field. Facial nerve monitoring leads are placed and utilized throughout the procedure. The ear is then prepped and draped in a sterile fashion. The incision is made sharply with a blade along the planned curvilinear line. The skin flaps are sharply elevated superficial to the temporalis fascia. Monopolar cautery is avoided and bipolar cautery is used for focal hemostasis. An anteriorly-based muscle and periosteal flap is designed, carried down to the bone, and elevated anteriorly as well as inferiorly to expose the bony external auditory meatus and the squamosa of the temporal bone.

A mini-craniotomy (2×2 cm) bone flap is marked and centered on the external auditory canal. The edges of the bone flap are drilled using both cutting and diamond burrs, and then the bone flap is elevated using a dental elevator, taking care to keep the middle fossa dura intact. Under the microscope or operative endoscope, the dura is gently elevated off the middle fossa floor. This proceeds in a posterior to anterior direction until the petrous ridge of the temporal bone is identified. This bony ledge is followed until the arcuate eminence of the superior semicircular canal is identified. A retractor may be placed at this time to expose the canal dehiscence to enable the repair. Frequently the dehiscence is out of view and can only be visualized with an angled endoscope.

The canal is then repaired using an occluding or resurfacing technique. The durability of repair is tested using a flush of saline irrigation. If a dehiscence is small or visible through extremely thinned (but present) bone, a 1.5 mm diamond burr at low speed (5000 RPM) is used to un-roof the defect to the membranous labyrinth layer, and then the defect is occluded or resurfaced. The retractor is then removed, the craniotomy defect closed with small miniplates and the soft tissue is closed in a layered fashion. Drainage of the wound is not necessary. The patient is cleaned and a mastoid dressing is applied. The patient is awoken from general anesthesia and observed in the hospital overnight. The dressing stays in place for five days. Symptom improvement following surgery is expected in the immediate post-operative period.

Once the dehiscence is reached, and optionally surgically enlarged or smoothed, the prosthesis can be placed. For an occluding prosthesis, the prosthesis is placed through the dehiscence, into the superior semicircular canal, obliterating the membranous labyrinth. See, for example, FIGS. 2A and 2B. For a resurfacing prosthesis, the prosthesis is placed with the shallow anchor inserted into the dehiscence and with the wings brought into contact with the outer surface of the canal that rest along the skull base floor. See, for example, FIGS. 1A and 1B. Imaging, such as computed tomography, plain film X-ray, or magnetic resonance imaging, may be used to determine the success of the repair intraoperatively.

Once the occluding or the resurfacing prosthesis is positioned, any commonly used tissue or bone adhesive or securing agent can be added to hold the prosthesis in place. Examples of such agents include, but are not limited to, bone wax, bone cement, bone grafts, dural-matrix, synthetic collagen, temporalis fascia, and/or fibrin-based sealant.

Additionally, the posterior or lateral semicircular canals could be approached and repaired similarly. In some cases patients with recalcitrant benign positional vertigo (BPV) require surgical occlusion of their posterior canal. In this situation the mastoid is opened and the posterior canal drilled open. An occluding prosthesis could be placed using measurements from the canal taken at the time of surgery.

In another example, the horizontal (lateral) semicircular canal can be eroded by diseases within the middle ear and mastoid. In such cases a dehiscence of the canal may be identified preoperatively on CT scans or may be the result of disease dissection during surgery. An occluding or resurfacing prosthesis could similarly be used for such application.

Alternatives

Although a particular number, type and configurations of features have been described, other alternatives are possible.

Figure 8A:
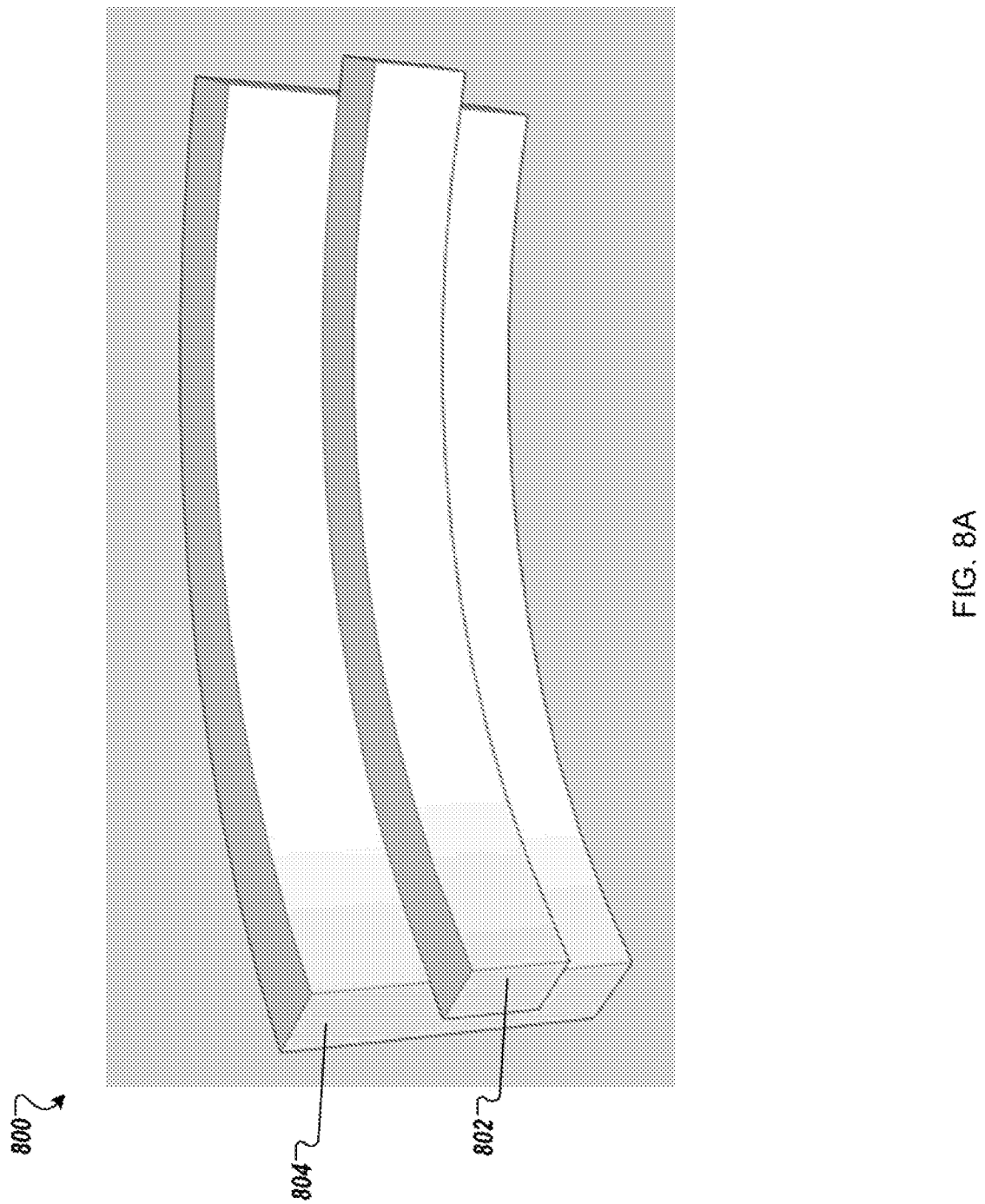
FIGS. 8A and 8B are schematic diagrams that shows examples of resurfacing prostheses that has alternative anchor sections.

In some examples, resurfacing prostheses can have an anchor of greater or lesser length than the wings section of the prosthesis. FIG. 8A shows an example of a resurfacing prosthesis 800 that has an anchor section 802 longer than the wings section 804. Such a resurfacing prosthesis can be useful, for example, in the case where the prosthesis does not readily sit within the lumen of the canal, and additional stability to position the prosthesis is needed.

Figure 8B:
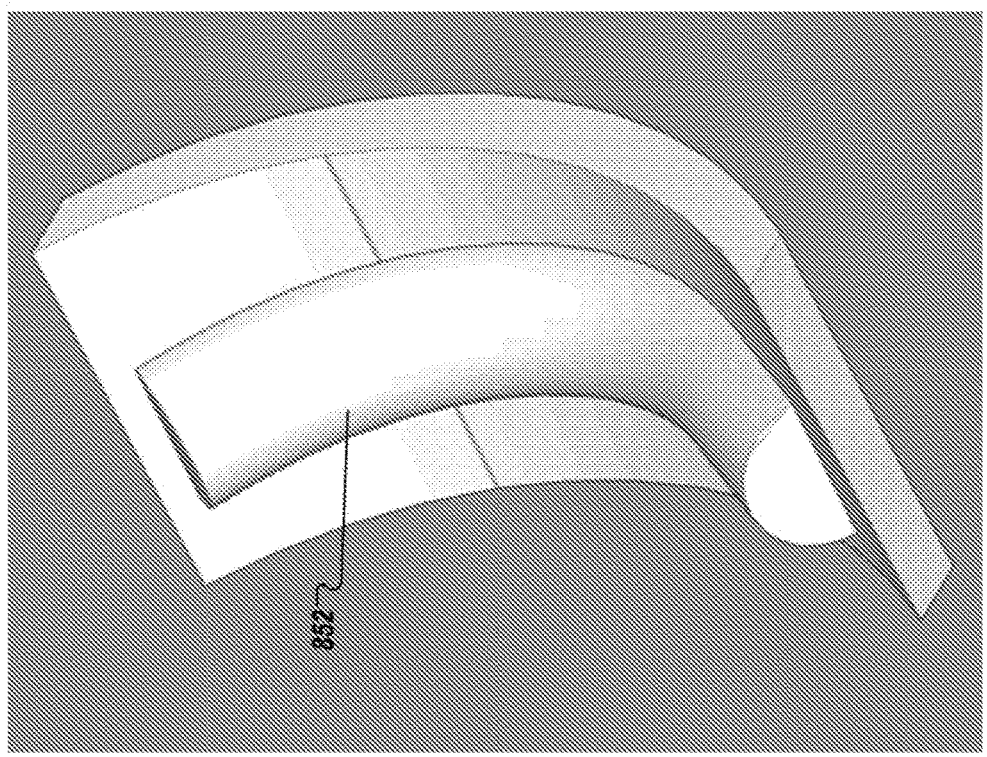

In some examples, the anchor of a resurfacing prosthesis may have a different cross-sectional shape. For example, instead of a rectangular cross-section, the anchor may have a circular, trapezoidal, or other shape. These shapes may be desirable, for example, to allow for press-fitting of the anchor in different shaped dehiscences. FIG. 8B shows an example of a resurfacing prosthesis 850 that has an anchor section 852 with a semi-circular cross section.

Figure 9A:
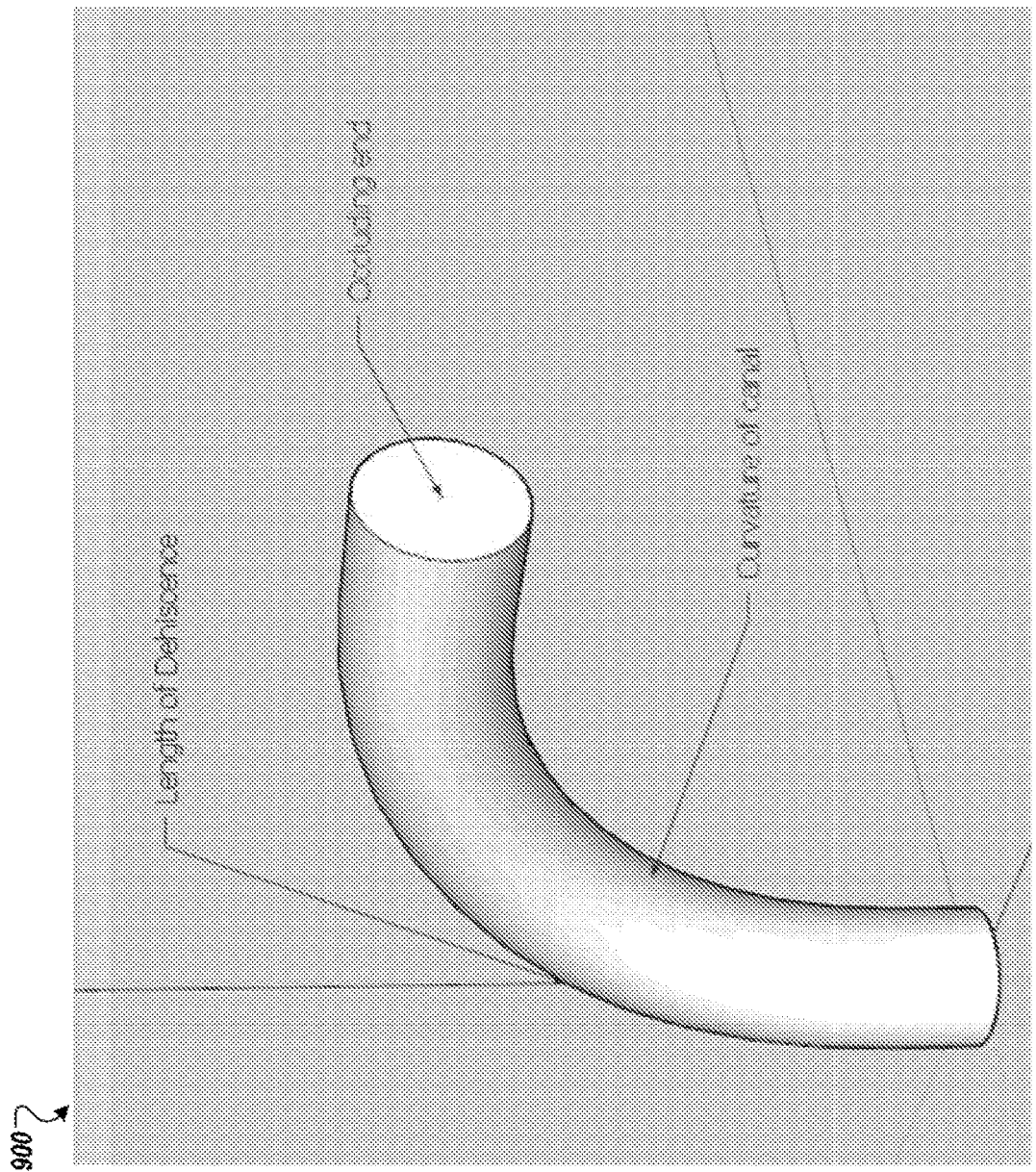
FIGS. 9A, 9B, and 9C are schematic diagrams that show examples of occluding prostheses with circular cross sections.
Figure 9B:
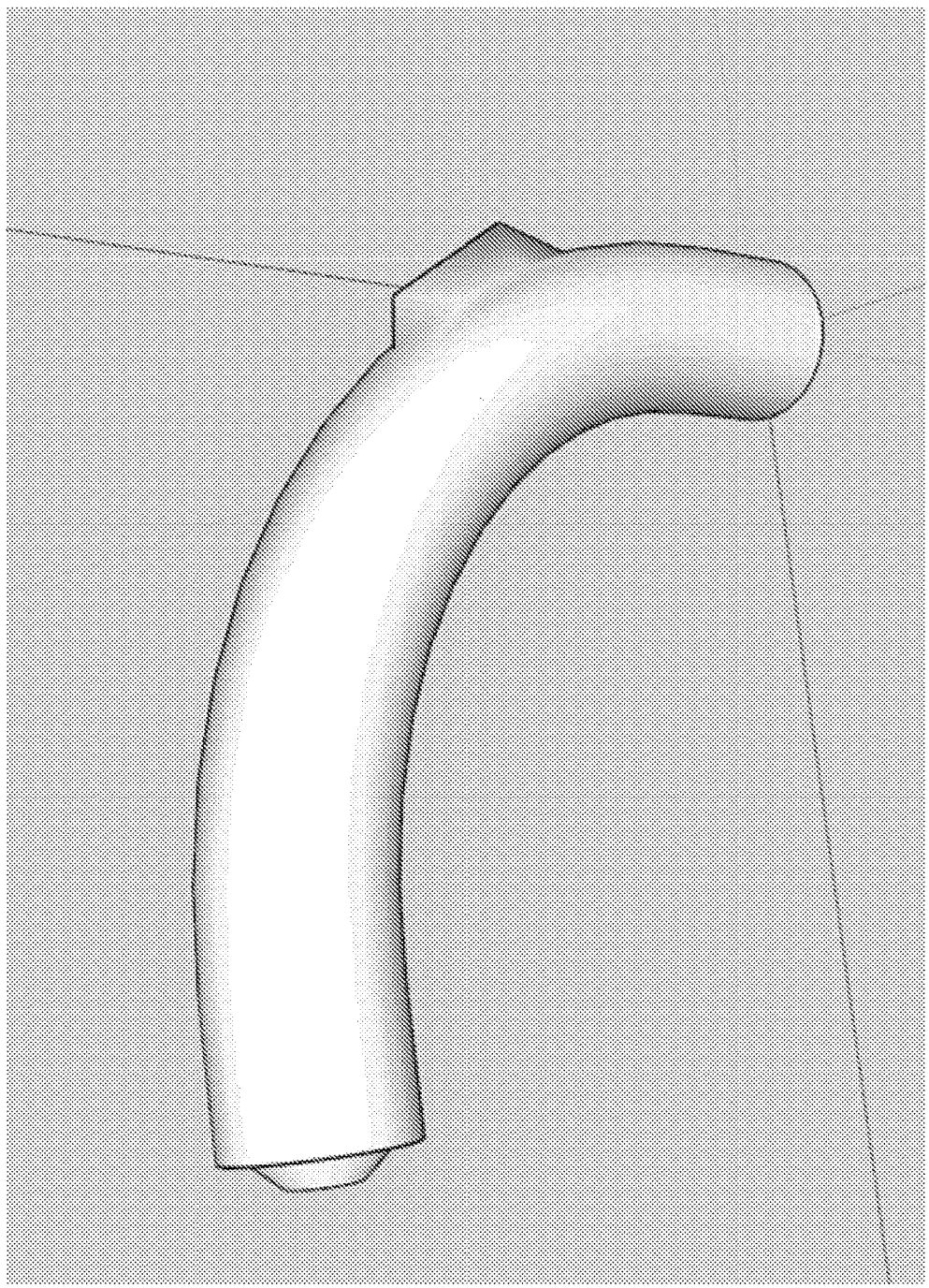
Figure 9C:
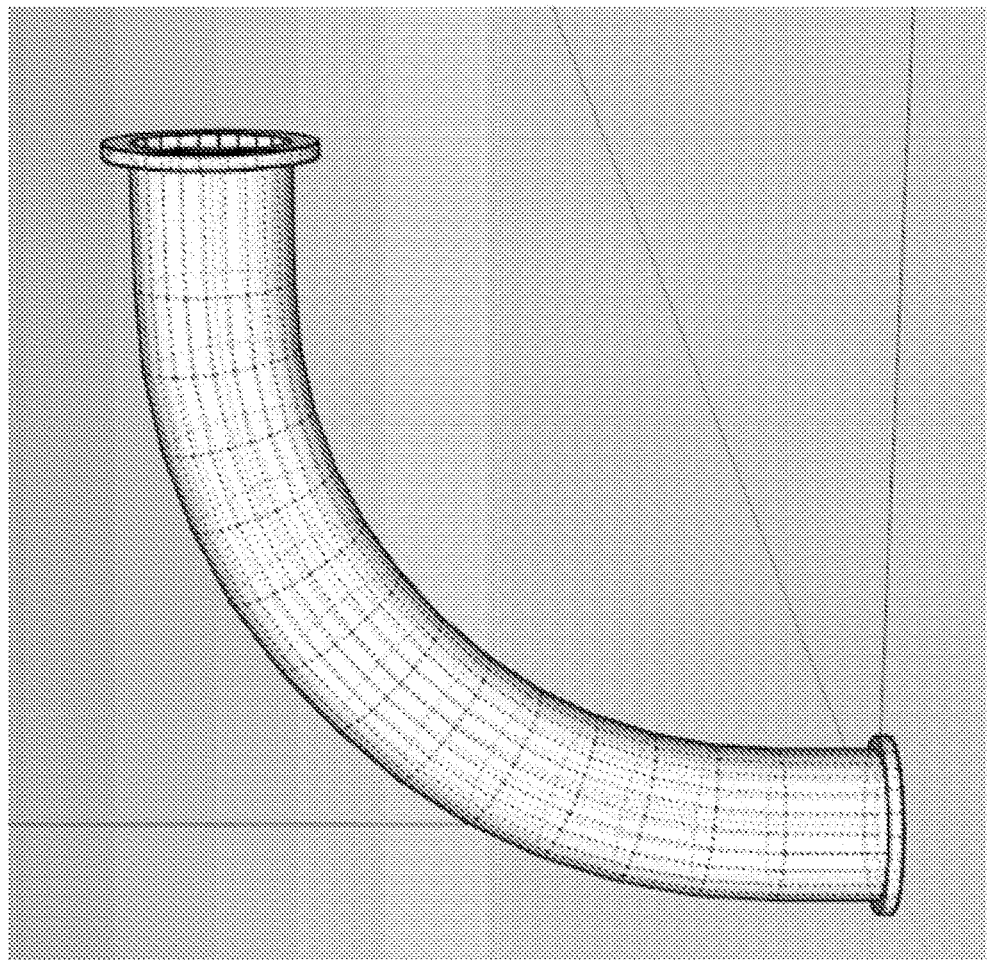

In some examples, occluding prostheses can have different cross-sections shapes. A trapezoidal shape has been previously described, but other shapes are possible. For example, occluding prostheses can have a different convex geometric shape such as rectangles, tubes, ovals, or circles, etc. FIGS. 9A, 9B, and 9C are schematic diagrams that show examples of occluding prostheses with circular cross-sections. FIG. 9A shows an occluding prosthesis 900 having a circular cross-section and flat faces. FIG. 9B shows an occluding prosthesis 925 having a circular cross-section and tapered faces. The tapered faces may be adjusted to fit canals of different proportions. The occluding prosthesis 925 also includes a handle for placement by a surgeon with, for example, forceps. FIG. 9C shows an occluding prosthesis 975 having enlarged endings for more robust occlusion of a canal, or for the canal that has flaring ends.

In some other examples, occluding prostheses can have a non-convex geometric shape. For example, a non-convex shape of superior semicircular canal can be captured in an image, and that non-convex shape can be used as the cross section of an occluding prosthesis.

In some examples, fabrication techniques other than 3D printing, or in addition to 3D printing can be used. For example, a 3D printed object can be used as an investment pattern in an investment casting process. In another example, prostheses can be fabricated by extruding a material through a die. In yet another example, a computer numerically controlled (CNC) fabrication machine (e.g., an end-mill) can cut a blank into a prosthesis device.

Figure 10:
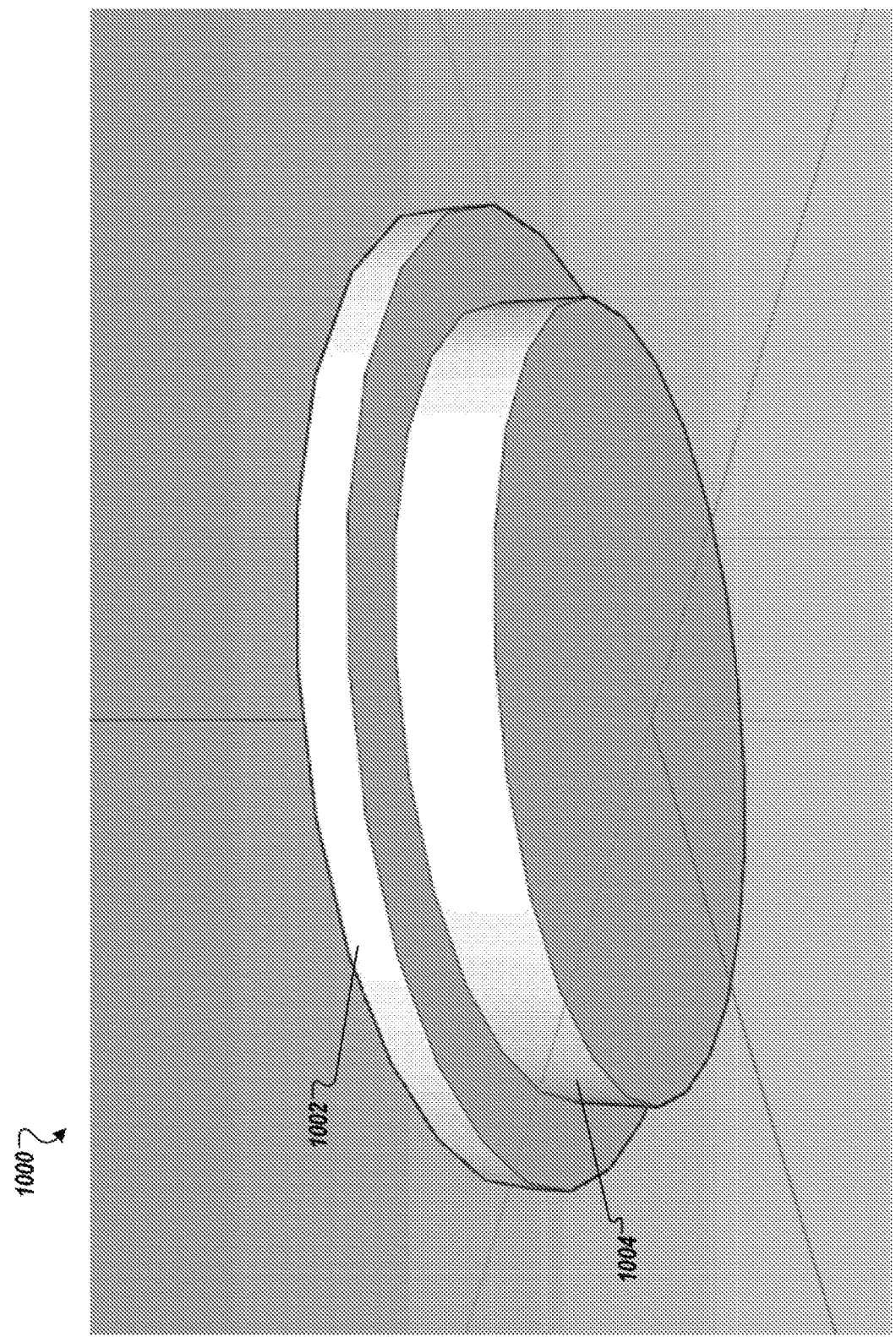
FIG. 10 is a schematic diagram that shows an example of a radial resurfacing prosthesis.

In some examples, a resurfacing prosthesis can have a radial shape, as opposed to a linear longitudinal axis. FIG. 10 shows an example of a radial resurfacing prosthesis 1000 having an anchor 1002 and a wings section 1004.

Figure 11:
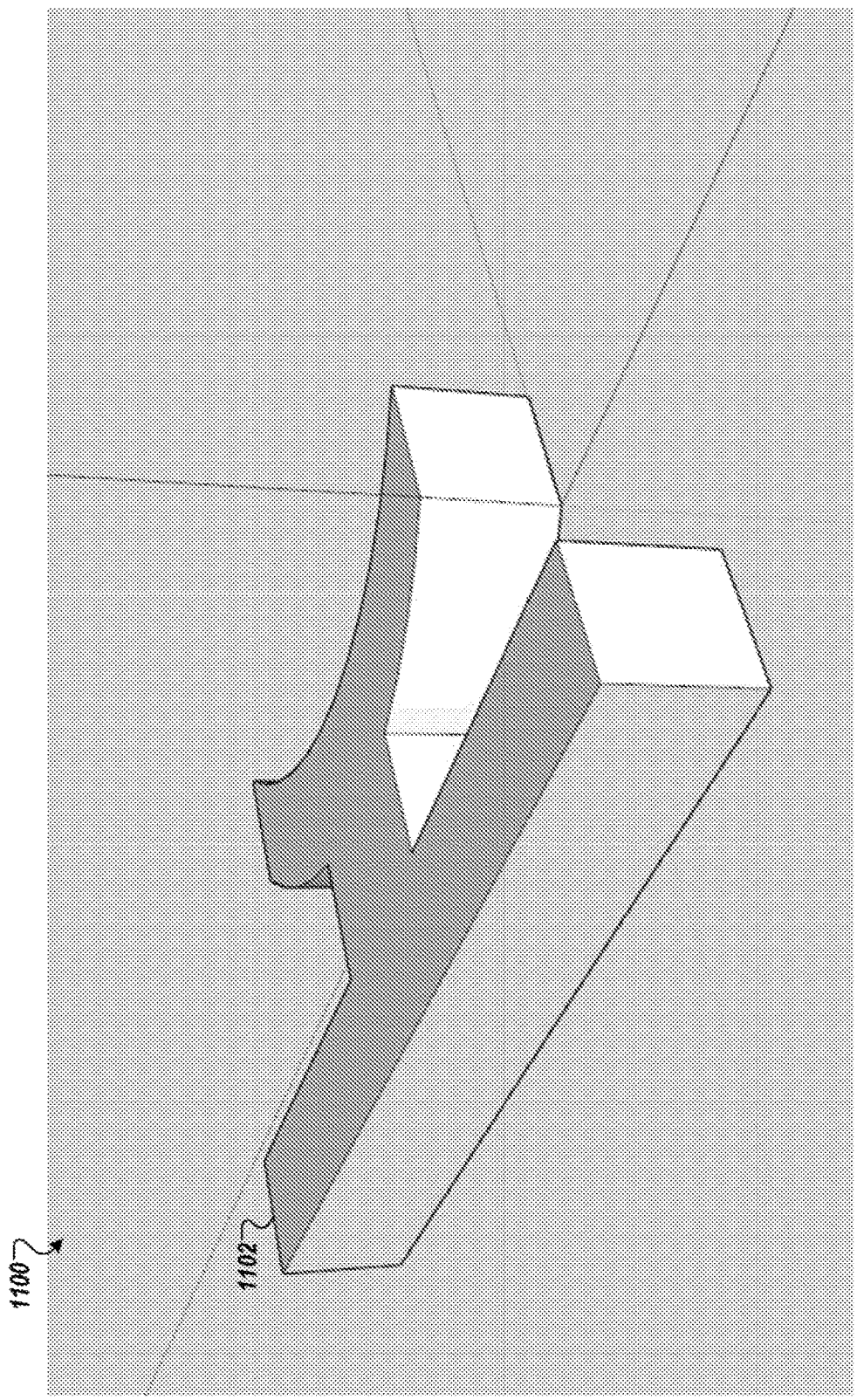
FIG. 11 is a schematic diagram that shows an example of an occluding prosthesis with a placement handle.

In some examples, a resurfacing prosthesis or an occluding prosthesis can have handles intended to aid in the placement of the prosthesis. FIG. 11 shows an example of an occluding prosthesis 1100 with a placement handle 1102. The occluding prosthesis 1100 can be handled and manipulated by the placement handle 1102 until the occluding prosthesis 1100 is placed in a dehiscence. Once placed, a user can remove the placement handle 1102, for example by cutting off the placement handle 1102 with a scalpel or scissor. The handle may be prefabricated to be easily removed intraoperatively. Alternatively, if using a prefabricated kit, 'sizers' of various shapes and lengths can serve to appropriately measure the defect after which point a prosthesis of an appropriate size is selected for implantation.

Figure 12:
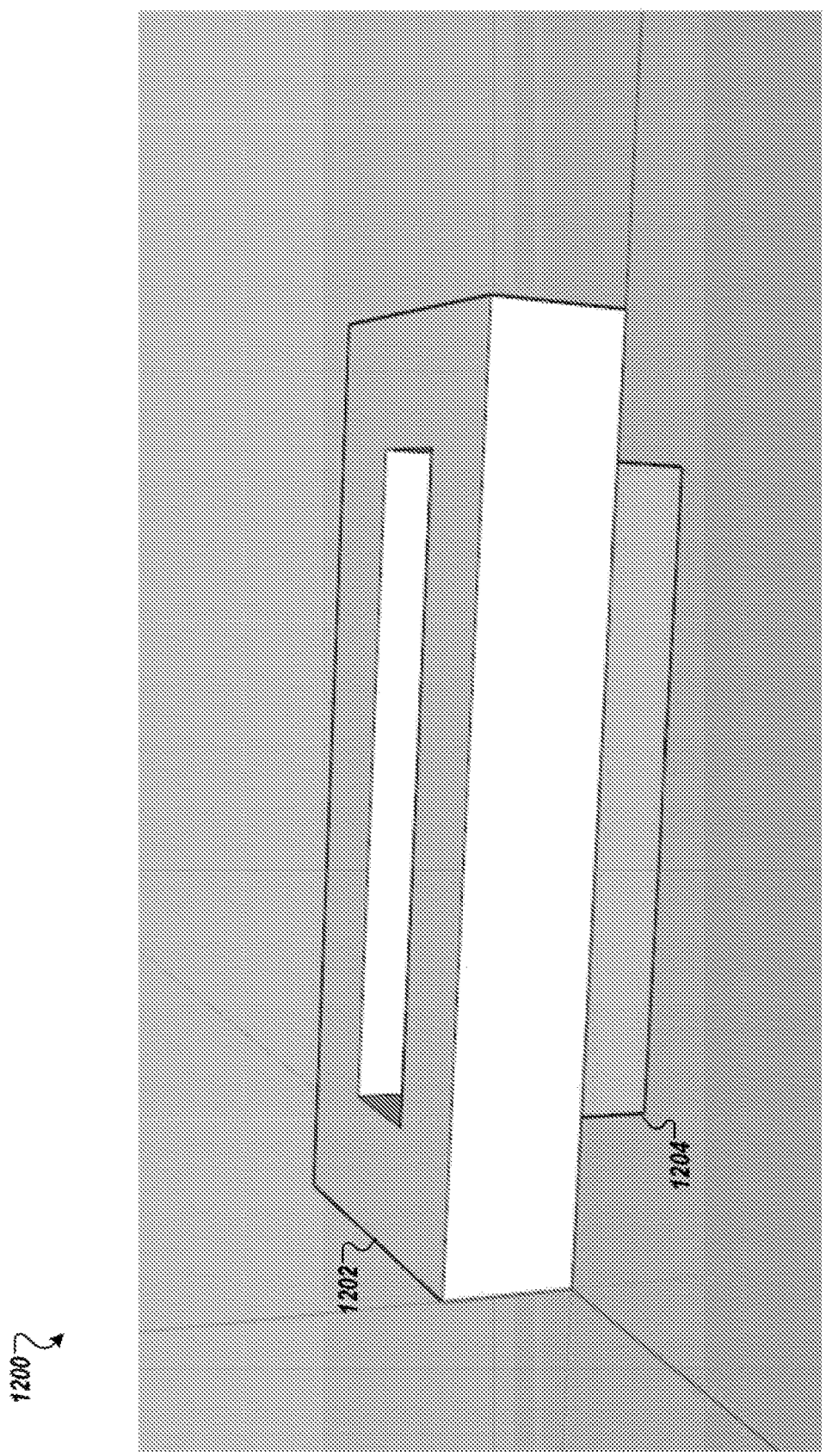
FIG. 12 is a schematic diagram that shows an example of a resurfacing prosthesis with wings surrounding the anchor section.

In some examples, a resurfacing prosthesis can have a wings section that surrounds the anchor section. FIG. 12 shows an example of a resurfacing prosthesis 1200 with wings 1202 surrounding the anchor section 1204.

Computer Systems

Figure 13:
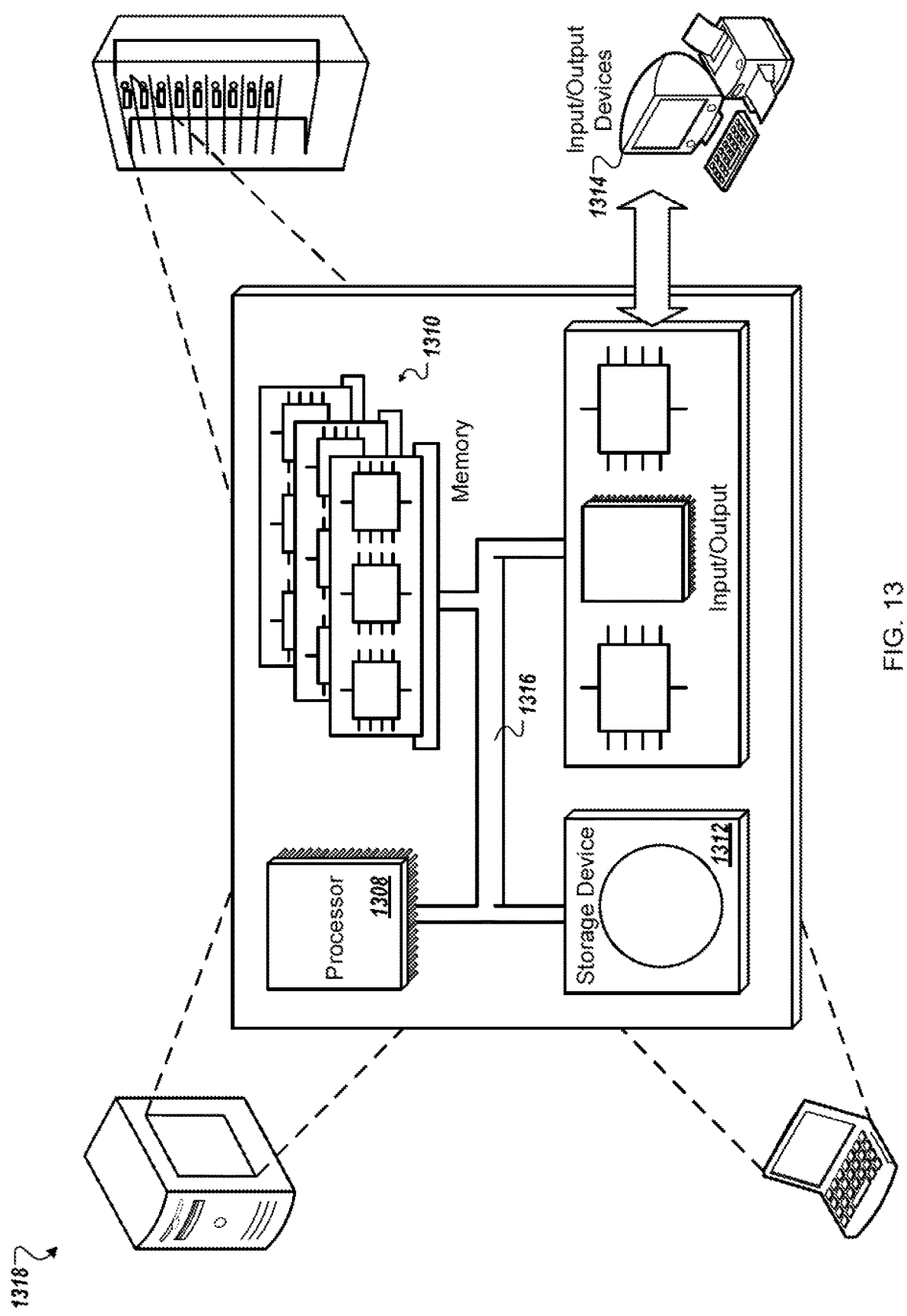
FIG. 13 is a schematic diagram that shows an example of a computing system.

FIG. 13 is a schematic diagram that shows an example of a computing system 1300 that can be used to carry out some or all of the operations and method steps described herein, e.g., according to the implementations described herein. The computing system 1300 includes a processor 1310, a memory 1320, a storage device 1330, and an input/output device 1340. Each of the processor 1310, the memory 1320, the storage device 1330, and the input/output device 1340 are interconnected using a system bus 1350. The processor 1310 is capable of processing instructions for execution within the computing system 1300. In some implementations, the processor 1310 is a single-threaded processor. In some implementations, the processor 1310 is a multi-threaded processor. The processor 1310 is capable of processing instructions stored in the memory 1320 or on the storage device 1330 to display graphical information for a user interface on the input/output device 1340.

The memory 1320 stores information within the computing system 1300. In some implementations, the memory 1320 is a computer-readable medium. In some implementations, the memory 1320 is a volatile memory unit. In some implementations, the memory 1320 is a non-volatile memory unit.

The storage device 1330 is capable of providing mass storage for the computing system 1300. In some implementations, the storage device 1330 is a computer-readable medium. In various different implementations, the storage device 1330 may be a floppy disk device, a hard disk device, an optical disk device, or a tape device.

The input/output device 1340 provides input/output operations for the computing system 1300. In some implementations, the input/output device 1340 includes a keyboard and/or pointing device. In some implementations, the input/output device 1340 includes a display unit for displaying graphical user interfaces.

Some features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM (erasable programmable read-only memory), EEPROM (electrically erasable programmable read-only memory), and flash memory devices; magnetic disks such as internal hard disks and removable disks; magneto-optical disks; and CD-ROM (compact disc read-only memory) and DVD-ROM (digital versatile disc read-only memory) disks. The processor and the memory can be supplemented by, or incorporated in, ASICs (application-specific integrated circuits).

To provide for interaction with a user, some features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

Some features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN (local area network), a WAN (wide area network), and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Example—Drug Release Testing

As described herein, a prosthesis can be manufactured to elute or release an active agent, such as a drug, e.g., over time. For example, such drugs may reduce the risk of infection and/or inhibit further hearing loss. To test the ability of the semicircular canal prostheses described herein to provide a sustained release of an active agent, three degradable polymers, Poly (d-l,lactide) (PDLLA), Poly vinyl acetate (PVAc), and Polycaprolactone (PCL) were dissolved in solvents ethyl acetate, methyl ethyl ketone (MEK), and toluene, respectively, and used to coat test prostheses.

Figure 14A:
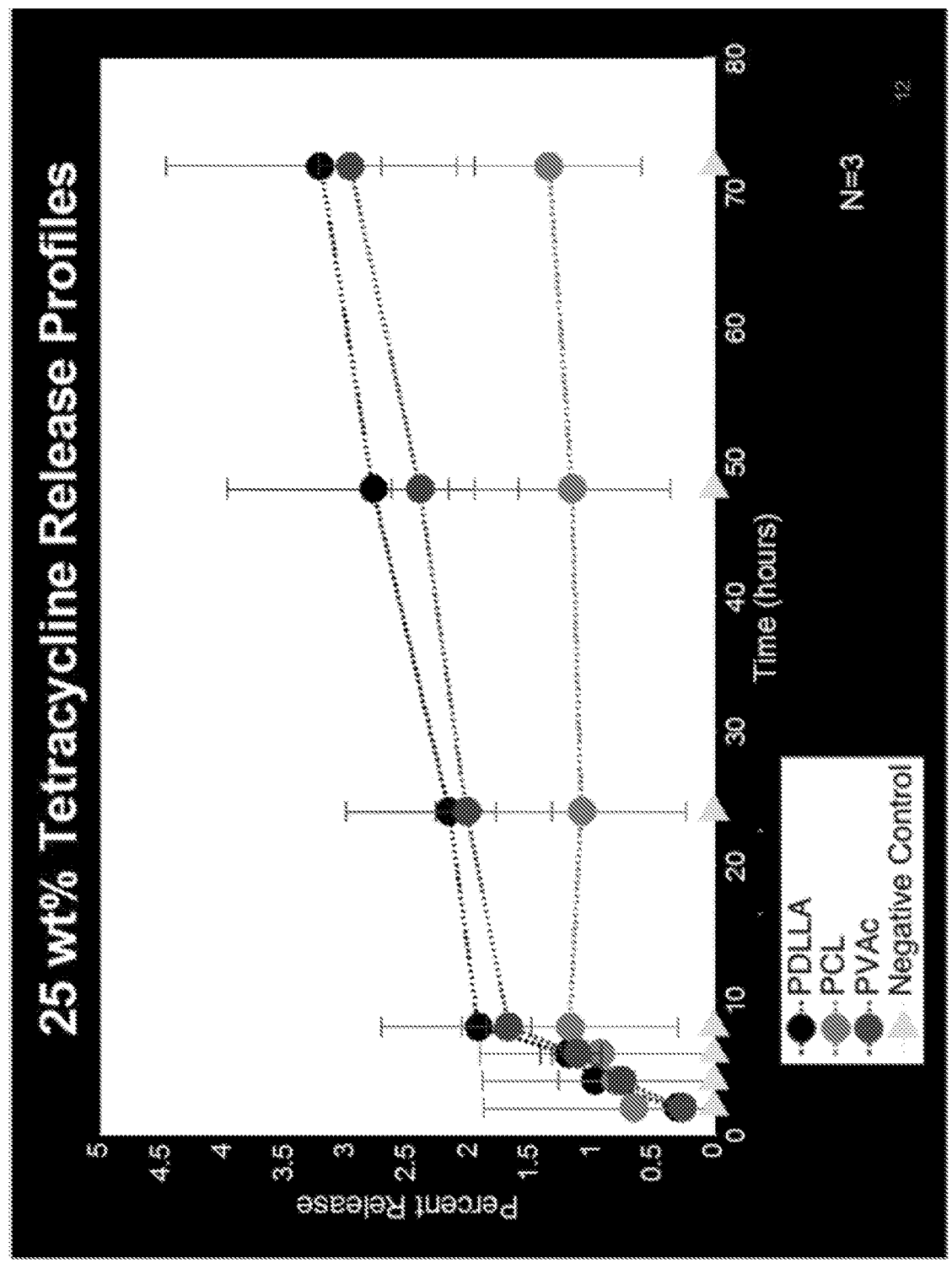
FIGS. 14A and 14B are graphs that show tetracycline release profiles over time from various examples of prostheses made using the methods and techniques described herein.
Figure 14B:
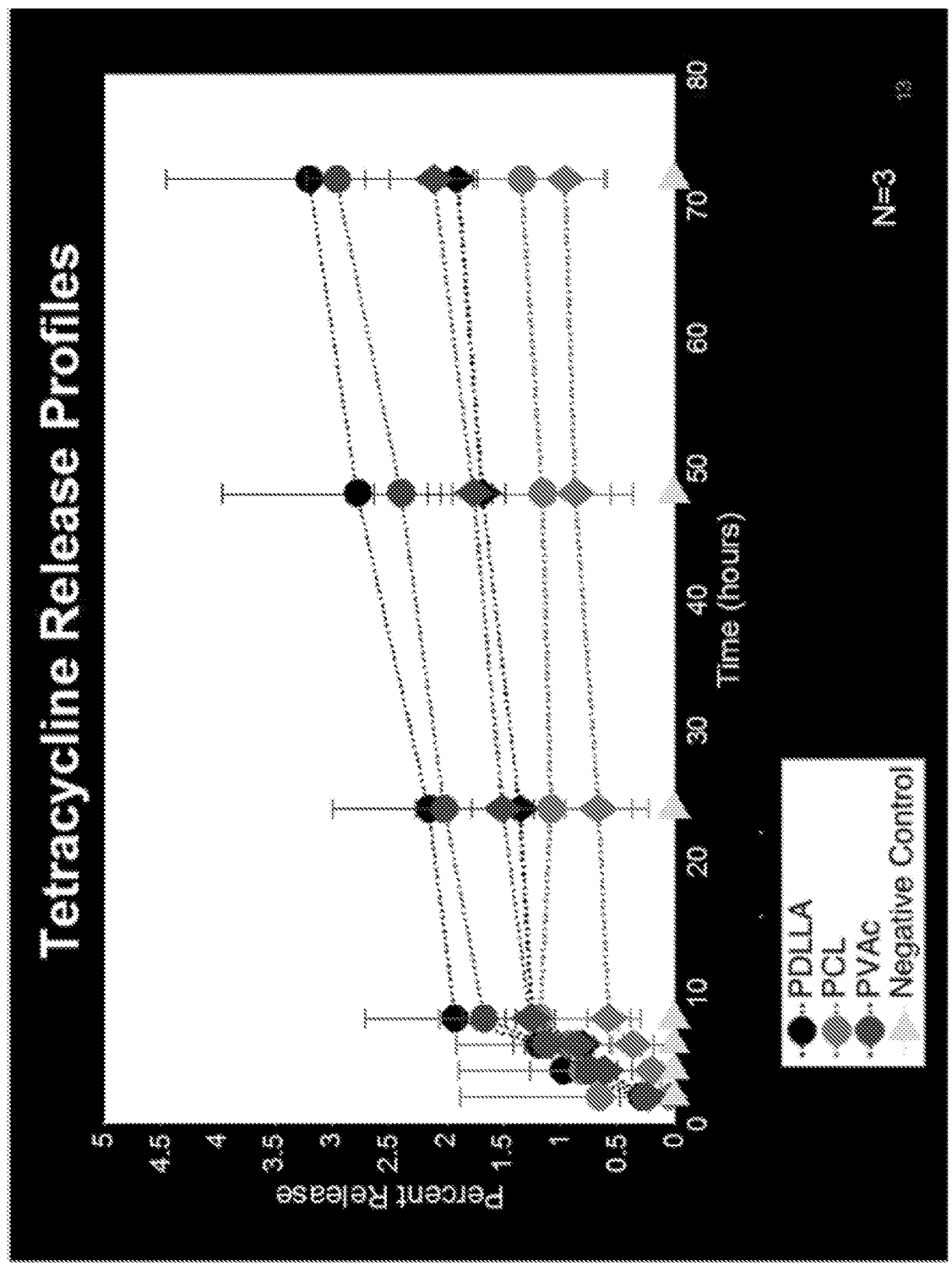

The drug tetracycline was mixed into each polymer solution at either 10 wt % (low concentration) or 25 wt % (high concentration). Test prostheses were dipped into the high concentration tetracycline-polymer solutions and allowed to dry. Half of the test prostheses where then also coated with a second coating of the low concentration solution. Prostheses were tested at various time points following placement in physiological media that simulates the extracellular fluid matrix of the skull base. The rate at which the drug is released into the surrounding media from the prosthesis can be measured. Based upon the concentration of drug and the polymer coating used, the rate of medication release can be controlled as illustrated in FIGS. 14A and 14B. The test prostheses where placed in sterile phosphate-buffered saline in a shaking incubator and media was changed at specific time points. Drug concentration was quantified using florescence.

FIG. 14A shows the release of the high concentration tetracycline-polymer coating over time. As shown, PDLLA had the highest release of the tetracycline, with PVAc in a near second. In all three cases, there is an initial bolus release followed by a slower gradual release over time.

FIG. 14B shows that for all three polymers, the second, low concentration coating slowed the release of the tetracycline. PVAC and PDLLA were grouped together with PCL having a slower release. In this test, the most viscous coating (PCL) with the largest dosage was the slowest to release.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An elongated semicircular canal prosthetic device having a T-shaped cross section comprising an anchor portion and a wing portion and having a curved longitudinal axis when viewed from a side of the device and a generally straight longitudinal axis and a rectangular shape when viewed in a plane perpendicular to the wing portion,
wherein the prosthetic device has a length of up to and including one centimeter;
wherein the anchor portion comprises a stem of the T-shaped cross section and extends along the curved longitudinal axis for at least a portion of the device;
wherein the wing portion comprises a horizontal top of the T-shaped cross section and extends along the curved longitudinal axis for at least a portion of the device;
wherein the wing portion comprises a lower concave surface that is configured, curved, and dimensioned to generally align with an outer surface of a semicircular canal bone;
wherein the anchor portion is narrower than the wing portion; and
wherein the anchor portion of the prosthetic device is configured and dimensioned to be seated in a defect of an outer bone of the semicircular canal without occluding a lumen of the semicircular canal when the device is seated in the defect.

2. The prosthetic device of claim 1, wherein the anchor portion is configured to be seated in the defect; and the wing portion is configured to be wider than the defect such that the wing portion is not able to fit within the defect.

3. The prosthetic device of claim 1, wherein the anchor portion comprises an outer surface configured to align with an inner surface of the defect to seal or resurface the defect in the semicircular canal.

4. The prosthetic device of claim 1, wherein the prosthetic device comprises a material that can store and elute one or more agents into one or more of surrounding bone, blood, inner ear, or tissue once the device is implanted in a patient, wherein the one or more agents comprise at least one of a steroid, antibiotic, bisphosphonate, anesthetic agent, lidocaine, non-steroidal anti-inflammatory, immunomodulating drug, biologic drug, tumor necrosis factor (TNF) inhibitor, interleukin (IL)-6 inhibitor, IL-1 inhibitor, T cell mediator, an antibody, a chemotherapy agent, cyclosporine, methotrexate, glutamate antagonist, memantine, caroverine, magnesium, neurotropic factor, NeuroTrophin-3, and brain-derived neurotropic factor (BDNF).

5. The prosthetic device of claim 1, wherein the prosthetic device comprises at least one of polydimethylsiloxane (PDMS), hyaluronic acid (HA), poly(glycolic acid) (PGA), poly (lactic-co-glycolic acid) (PLGA), polylactic acid (PLA), polyurethane, collagen, fibrin, nylon, silk, poliglecaprone, elastin, titanium, platinum, aluminum, metal alloys, metal composites, or nitinol.

6. The prosthetic device of claim 1, wherein the prosthetic device comprises a radiopaque material.

7. The prosthetic device of claim 1, wherein the defect is a dehiscence.

8. A method of generating a geometric model of a semicircular canal defect for a specific patient and fabricating a corresponding prosthetic device for the specific patient, the method comprising:
receiving, by a computer system, first data comprising one or more images of a defect in a semicircular canal of the specific patient;
generating, by the computer system, second data from the first data, wherein the second data comprises one or more measurements of the defect;
generating, by the computer system, third data from the second data, wherein the third data comprises one or more prosthetic parameters that define at least some of the geometry of a prosthetic device for the specific patient;
generating, by the computer system, a geometric model of the prosthetic device from the third data;
outputting, by the computer system, the geometric model for fabrication; and
fabricating the prosthetic device using the geometric model, wherein the prosthetic device has a T-shaped cross section comprising an anchor portion and a wing portion and a curved longitudinal axis when viewed from a side of the device and a generally straight longitudinal axis and a rectangular shape when viewed in a plane perpendicular to the wing portion,
wherein the prosthetic device has a length of up to and including one centimeter;
wherein the anchor portion comprises a stem of the T-shaped cross section and extends along the curved longitudinal axis for at least a portion of the device;
wherein the wing portion comprises a horizontal top of the T-shaped cross section and extends along the curved longitudinal axis for at least a portion of the device;
wherein the wing portion comprises a lower concave surface that is configured, curved, and dimensioned to generally align with an outer surface of a semicircular canal bone;
wherein the anchor portion is narrower than the wing portion; and
wherein the anchor portion of the prosthetic device is configured and dimensioned to be seated in the semicircular canal defect without occluding a lumen of the semicircular canal when the device is seated in the defect.

9. The method of claim 8, wherein the method comprises fabricating the prosthetic device using three-dimensional (3D) printing.

10. The method of claim 8, wherein the one or more images of the first data comprise at least one of a Pöschl view of the defect and a Stenvers view.

11. The method of claim 8, wherein the one or more measurements of the defect comprise at least one of a curve of the defect, a depth of the defect, and a width of the defect, and wherein the one or more prosthetic parameters comprise at least one of a curved longitudinal axis, a prosthetic depth, or a prosthetic width.

12. The method of claim 11, wherein:
the one or more measurements of the defect comprise a curve of the defect, a depth of the defect, and a width of the defect; and
the one or more prosthetic parameters comprise a curved longitudinal axis that corresponds to the curve of the defect, a prosthetic depth that corresponds to the depth of the defect, and a prosthetic width that corresponds to the width of the defect.

13. The method of claim 8, wherein generating the geometric model further comprises programmatically generating the geometric model using the third data as input.

14. A method of 3D printing a semicircular canal prosthetic device, the method comprising:
receiving a build plan for a prosthetic device having a T-shaped cross section comprising an anchor portion and a wing portion and having a curved longitudinal axis when viewed from a side of the device and a generally straight longitudinal axis and a rectangular shape when viewed in a plane perpendicular to the wing portion, wherein the prosthetic device has a length of up to and including one centimeter;

wherein the anchor portion comprises a stem of the T-shaped cross section and extends along the curved longitudinal axis for at least a portion of the device;

wherein the wing portion comprises a horizontal top of the T-shaped cross section and extends along the curved longitudinal axis for at least a portion of the device;

wherein the wing portion comprises a lower concave surface that is configured, curved, and dimensioned to generally align with an outer surface of a semicircular canal bone;

wherein the anchor portion is narrower than the wing portion; and wherein the anchor portion of the prosthetic device is configured and dimensioned to be seated in a defect of a semicircular canal without occluding a lumen of the semicircular canal when the device is seated in the defect; and 3D printing the prosthetic device according to the build plan.

15. The method of claim 14, wherein the anchor portion is configured to be seated in the defect; and the wing portion is configured to be wider than defect such that the wing portion is not able to fit within the defect.

16. The method of claim 14, wherein the anchor portion comprises an outer surface configured to align with an inner surface of the defect to seal or resurface the defect in the semicircular canal.

* * * * *